(12) United States Patent
Guilak et al.

(10) Patent No.: US 9,649,409 B2
(45) Date of Patent: May 16, 2017

(54) TISSUE ENGINEERING METHODS AND COMPOSITIONS

(71) Applicant: Cytex Therapeutics, Inc., Durham, NC (US)

(72) Inventors: Farshid Guilak, Durham, NC (US); Bradley T. Estes, Durham, NC (US); Franklin Thomas Moutos, Raleigh, NC (US)

(73) Assignee: Cytex Therapeutics, Inc., Durham, NC (US)

( * ) Notice: Subject to any disclaimer, the term of this patent is extended or adjusted under 35 U.S.C. 154(b) by 0 days.

(21) Appl. No.: 14/246,677

(22) Filed: Apr. 7, 2014

(65) Prior Publication Data
US 2014/0227336 A1  Aug. 14, 2014

Related U.S. Application Data

(63) Continuation of application No. 12/083,619, filed as application No. PCT/US2006/035243 on Sep. 11, 2006, now Pat. No. 8,691,542.
(Continued)

(51) Int. Cl.
| | | |
|---|---|---|
| A61F 2/30 | (2006.01) |
| A61F 2/32 | (2006.01) |
| A61F 2/38 | (2006.01) |
| A61F 2/40 | (2006.01) |
| A61F 2/42 | (2006.01) |
| A61F 2/44 | (2006.01) |
| A61L 27/54 | (2006.01) |
| A61K 35/28 | (2015.01) |
| C12N 5/0775 | (2010.01) |
| A61K 35/32 | (2015.01) |
| A61K 35/33 | (2015.01) |

(Continued)

(52) U.S. Cl.
CPC .............. *A61L 27/54* (2013.01); *A61K 35/28* (2013.01); *A61K 35/32* (2013.01); *A61K 35/33* (2013.01); *A61K 38/1841* (2013.01); *A61K 38/1875* (2013.01); *A61K 38/30* (2013.01); *C12N 5/0667* (2013.01); *A61K 35/12* (2013.01); *C12N 2501/105* (2013.01); *C12N 2501/11* (2013.01); *C12N 2501/115* (2013.01); *C12N 2501/135* (2013.01); *C12N 2501/15* (2013.01); *C12N 2501/155* (2013.01); *C12N 2501/23* (2013.01); *C12N 2501/37* (2013.01); *C12N 2501/39* (2013.01); *C12N 2533/30* (2013.01); *C12N 2533/40* (2013.01)

(58) Field of Classification Search
None
See application file for complete search history.

(56) References Cited

U.S. PATENT DOCUMENTS 5,711,960 A * 1/1998 Shikinami .................... 424/426
5,736,372 A * 4/1998 Vacanti et al. ................ 435/180

(Continued)

*Primary Examiner* — Elizabeth C Kemmerer
(74) *Attorney, Agent, or Firm* — Maginot, Moore & Beck, LLP

(57) ABSTRACT

Cells are employed in conjunction with unique biologically-compatible scaffold structures to generate differentiated tissues and structures, both in vitro and in vivo. The presently disclosed subject matter further relates to methods of forming and using improved tissue engineered scaffolds that can be used as substrates to facilitate the growth and differentiation of cells.

22 Claims, 8 Drawing Sheets

Related U.S. Application Data

(60) Provisional application No. 60/715,530, filed on Sep. 9, 2005, provisional application No. 60/724,044, filed on Oct. 6, 2005.

(51) Int. Cl.
*A61K 38/18* (2006.01)
*A61K 38/30* (2006.01)
*A61K 35/12* (2015.01)

(56) References Cited

U.S. PATENT DOCUMENTS 6,746,485 B1 * 6/2004 Zucherman et al. ...... 623/17.16
2004/0267362 A1 * 12/2004 Hwang et al. ............. 623/13.15

* cited by examiner

TISSUE ENGINEERING METHODS AND COMPOSITIONS

CROSS REFERENCE TO RELATED APPLICATIONS

This application is a divisional of co-pending application Ser. No. 12/083,619, now U.S. Pat. No. 8,691,542, filed on Apr. 8, 2014, which is a national stage application under 35 U.S.C. §371 of international application PCT/US2006/035243, filed on Sep. 11, 2006, which claims priority to U.S. Provisional Patent Application Ser. Nos. 60/715,530 and 60/724,044, filed Sep. 9, 2005 and Oct. 6, 2005, respectively, the disclosures of which are hereby incorporated by reference in their entireties.

GRANT STATEMENT

This work was supported by grants AR49494 and GM08555 from the United States National Institutes of Health. Thus, the U.S. government has certain rights in the presently disclosed subject matter.

TECHNICAL FIELD

The presently disclosed subject matter generally relates to novel methods and systems for differentiating adipose derived stem (ADS) cells to provide cells and tissues suitable for laboratory and therapeutic applications. These cells, and other cells, can be employed alone or in conjunction with unique biologically-compatible scaffold structures to generate differentiated tissues and structures, both in vitro and in vivo.

TABLE OF ABBREVIATIONS

| | |
|---|---|
| ADS | adipose-derived stem |
| ANOVA | analysis of variance |
| BaCl.sub.2 | barium chloride |
| BMI | body mass index |
| BMP | bone morphogenic protein |
| CaCl.sub.2 | calcium chloride |
| CAT | chloramphenicol acetyl transferase |
| cm | centimeter |
| CMV | cytomegalovirus |
| COMP | cartilage oligomeric protein |
| Dhfr | dihydrofolate reductase |
| DMEM | Dulbecco's Modified Eagle's Medium |
| DNA | deoxyribonucleic acid |
| dsDNA | double stranded DNA |
| EG | embryonic germ |
| EGF | epidermal growth factor |
| ePTFR | expanded PTFE |
| ES | embryonic stem |
| FACS | fluorescence-activated cell sorting |
| FBS | fetal bovine serum |
| FGF | fibroblast growth factor |
| g | gram |
| GAG | glycosaminoglycan |
| GF | growth factor |
| GFP | green fluorescent protein |
| GLA | glycine leucine alanine |
| hADS | human adipose-derived stem |
| Hprt | hypoxanthine phosphoribosyl transferase |
| HSC | hematopoietic stem cells |
| HSV-tk | herpes simplex virus-thymidine kinase |
| IEp | immediate early viral promoter |
| IGF-I | insulin-like growth factor |
| ITR | inverted terminal repeat |
| L | liter |
| LTR | long terminal repeat |
| mg | milligram |
| mL | milliliter |

TABLE OF ABBREVIATIONS -continued

| | |
|---|---|
| MLV | murine leukemia virus |
| mM | millimolar |
| mRNA | messenger RNA |
| MSC | mesenchymal stem cell |
| NaCl | sodium chloride |
| ng | nanogram |
| p | probability |
| PBS | phosphate buffered saline |
| PCR | polymerase chain reaction |
| PEEK | polyetheretherketone |
| PEG | polyethylene glycol |
| PEO | polyethylene oxide |
| PGA | polyglycolic acid |
| PDGF | platelet-derived growth factor |
| Pgk | phosphoglycerate kinase |
| PLA | processed lipoaspirate |
| PLSD | protected least significant difference |
| PTFE | polyetetrafluoroethylene |
| PTHrP | parathyroid hormone-related protein |
| RGD | arginine glycine aspartic acid |
| RNA | ribonucleic acid |
| RSV | rous sarcoma virus |
| S.E.M. | standard error of measurement |
| SV40 | simian virus 40 |
| TAF | transcription associated factor |
| TGF-α | transforming growth factor α |
| TGF-β | transforming growth factor β |
| VEGF | vascular endothelial growth factor |
| 2-D | 2-dimensional |
| 3-D | 3-dimensional |
| $^3$H | tritium |
| μCi | microcuries |
| μg | microgram |
| μm | micrometer |
| % | percent |
| # | number |
| ≤ | less than or equal to |
| ≥ | greater than or equal to |
| > | greater than |
| < | less than |
| = | equal to |
| ± | plus or minus |
| + | plus |

BACKGROUND

Many disease conditions or injuries of the body require the repair or replacement of damaged tissues and/or structures, but the body itself may not be able to replace or repair the tissue and/or structures satisfactorily or within an appropriate time scale. Accordingly, many methods of disease or injury treatment involve augmenting the body's natural repair mechanisms and often rely on the use of implantable biological scaffolds or prostheses. Tissue engineering attempts to create three-dimensional tissue structures on which cells and other biomolecules can be incorporated. These structures or scaffolds guide the organization, growth and differentiation of cells in the process of forming functional tissue by providing physico-chemical cues.

For example, degenerative joint diseases such as osteoarthritis remain a source of significant pain and disability, resulting in an economic burden of over 40 billion dollars per year to the United States. Present treatment options for osteoarthritis are limited, and surgical management generally involves replacement of the joint with a metal and polyethylene prosthesis. The short life span and loading tolerance of joint replacement makes this treatment unacceptable for young, potentially active individuals. The treatment of synovial joints using tissue engineered grafts shows tremendous promise but its application has been limited to the treatment of small cartilage defects in the knee joint.

Further, articular cartilage is avascular, aneural, and has limited capacity for self-repair. Particularly, articular cartilage is a thin layer of soft connective tissue (0.5-5 mm thick) that covers the articulating surfaces of long bones in synovial joints. The principal function of articular cartilage is to redistribute applied loads and to provide a low friction-bearing surface to facilitate movement within these joints. Damage to this connective tissue in joints results in significant pain and morbidity, and currently, there are few options available for treatment. Some treatment options include lavage, debridement, microfracture, and autologous and/or allogeneic osteochondral/chondral grafts (reviewed in Hunziker (2002) *Osteoarthritis Cartilage* 10:432-463.

The success rates from these treatment options vary greatly, and some show promise. However, in many of the studies, the results suggest fibrous tissue formation, apoptosis, and further cartilage degeneration nonetheless occur (Furukawa et al. (1980) *J Bone Joint Surg Am* 62:79-89; Kim et al. (1991) *J Bone Joint Surg Am* 73:1301-1315; Shapiro et al. (1993) *J Bone Joint Surg Am* 75:532-553; Nehrer et al. (1999) *Clin Orthop Relat Res* 365:149-162; Tew et al. (2000) *Arthritis Rheum* 43:215-225; Mitchell and Shephard (2004) *Clin Orthop Relat Res* 423:3-6. Autologous chondrocyte transplants studies have also shown an inability to produce hyaline cartilage repair tissue, specifically over long time periods Brittberg et al. (1996) *Clin Orthop Relat Res* 326:270-283; Brittberp (1999) *Clin Orthop Relat Res* 367(Suppl):S147-155; Nehrer et al. (1999) *Clin Orthop Relat Res* 365:149-162; Breinan et al. (2001) *J Orthop Relat Res* 19:482-492, and even though some clinical studies have shown some promising results Brittberg et al. (1994) *N Engl J Med* 331:889-895; Breinan et al. (1997) *J Bone Joint Surg Am* 79:1439-1451; Minas and Nehrer (1997) *Orthopedics* 20:525-538; Gillogly et al. (1998) *J Orthop Sports Phys Ther* 28:241-251, as with the other treatment options, randomized, controlled trials are needed to truly ascertain the efficacy of these procedures. Given the success rate to date of current cartilage remodeling, repair, regrowth, and/or regeneration treatment options, combined with the burgeoning economic burden cartilage pathology and osteoarthritis has on society (Jackson et al. (2001) *Clin Orthop Relat Res* 391(Suppl):S14-25), novel tissue engineering approaches are needed to establish improved options for the treatment of cartilage defects and osteoarthritis, among other maladies.

In recent years, the identification of mesenchymal stem cells has led to advances in tissue regrowth and differentiation. Such cells are pluripotent cells found in bone marrow and periosteum, capable of differentiating into various mesenchymal or connective tissues. For example, such bone-marrow derived stem cells can be induced to develop into myocytes upon exposure to agents such as 5-azacytidine (Wakitani et al., (1995) *Muscle Nerve,* 18(12), 1417-26). It has been suggested that such cells are useful for repair of tissues such as cartilage, fat, and bone (see, e.g., U.S. Pat. Nos. 5,908,784, 5,906,934, 5,827,740, 5,827,735), and that they also have applications through genetic modification (see, e.g., U.S. Pat. No. 5,591,625). While the identification of such cells has led to advances in tissue regrowth and differentiation, the use of such cells is hampered by several technical hurdles. One drawback to the use of such cells is that they are very rare (representing as few as 1/2,000,000 cells), making any process for obtaining and isolating them difficult and costly. Additionally, bone marrow harvest is universally painful to the donor. Moreover, such cells are difficult to culture without inducing differentiation, unless specifically screened sera lots are used, adding further cost and labor to the use of such stem cells. Thus, there is a need for a more readily available source for pluripotent stem cells, particularly cells that can be cultured without the requirement for costly prescreening of culture materials.

Other advances in tissue engineering have shown that cells can be grown in specially-defined cultures to produce three-dimensional structures. Spatial definition typically is achieved by using various acellular fiber scaffolds or matrices to support and guide cell growth and differentiation. While this technique is still in its infancy, experiments in animal models have demonstrated that it is possible to employ various acellular fiber scaffold materials to regenerate whole tissues (see, e.g., Probst et al. (2000) *BJU Int.,* 85(3), 362-367). While artificial fiber scaffolds have been developed, these can prove toxic either to cells or to patients when used in vivo, or do not provide adequate mechanical support required for tissue repair. Accordingly, there remains a need for a scaffold material suitable for use as a substrate in culturing and growing populations of cells, wherein the matrix, cell combination is tailored specifically for replacement of a target tissue. Ultimately, this replacement tissue will serve to substantially function as the native tissue it seeks to replace.

Accordingly, the presently disclosed subject matter addresses needs in the art for improved methods for producing improved tissue engineered implantable compositions. This and other needs are addressed in whole or in part by the presently disclosed subject matter.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

Methods and compositions for treating a tissue pathology in a subject are disclosed. In some embodiments, the subject is a mammalian subject.

In some embodiments, the method comprises providing to an adipose-derived stem (ADS) cell in culture; exposing the ADS cell to an effective amount of a BMP-6 polypeptide or a functional fragment thereof, wherein the effective amount of the BMP-6 polypeptide or the functional fragment thereof is sufficient to induce the ADS cell to differentiate into a cell capable of treating the tissue pathology in the subject; administering the cell to the subject. In some embodiments, the effective amount of BMP-6 ranges from about 1 picogram/mL to about 10 milligram/mL.

Also disclosed is a method for treating a tissue pathology in a subject, comprising providing to an adipose-derived stem (ADS) cell in culture; exposing the ADS cell to an effective amount of a biologically active agent, wherein the effective amount of the biologically active agent is sufficient to induce the ADS cell to differentiate into a cell capable of treating the tissue pathology in the subject; and administering the cell to the subject.

Also disclosed is a composition for treating a tissue pathology in a subject. The composition can comprise an adipose-derived stem (ADS) cell that has been differentiated in vitro by exposure to an effective amount of a BMP-6 polypeptide or a functional fragment thereof; and a pharmaceutically acceptable carrier or excipient.

Also disclosed is composition for treating a tissue pathology in a subject, the composition comprising an adipose-derived stem (ADS) cell; an effective amount of a BMP-6 polypeptide or a functional fragment thereof; and a pharmaceutically acceptable carrier or excipient.

Also disclosed is a composition for treating a tissue pathology in a subject, the composition comprising an adipose-derived stem (ADS) cell that has been differentiated in vitro by exposure to an effective amount of a biologically active agent; and a pharmaceutically acceptable carrier or excipient.

Also disclosed is a composition for treating a tissue pathology in a subject, the composition comprising an adipose-derived stem (ADS) cell; an effective amount of a biologically active agent; and a pharmaceutically acceptable carrier or excipient.

The cell can be administered to a target tissue selected from the group including but not limited to articular cartilage, non-articular cartilage, auricular cartilage, tracheal cartilage, laryngeal cartilage, nasal cartilage, growth plate cartilage, meniscus, labrum, intervertebral disc, tendon, ligament, periodontal ligament, fascia, and muscle. The target tissue can comprise multiple tissue types that are integrated with one another selected from the group consisting of bone and cartilage, muscle and tendon, and ligament and bone. The tissue pathology can comprise a compromise in the normal homeostasis of the tissue, optionally culminating in degeneration of the tissue. The tissue pathology can comprise loss, damage, injury, or combinations thereof to the tissue. The treating can comprise tissue remodeling, repair, regrowth, resurfacing, regeneration, or combinations thereof.

The ADS cells from an adipose depot selected from the group can be selected from the group including but not limited to subcutaneous abdomen, thigh, buttocks, infrapatellar fat pad, and combinations thereof. The ADS cell can be selected from the group including but not limited ADS cells autologous to the subject, ADS cells allogeneic to the subject, ADS cells xenogenic to the subject, and combinations thereof.

The isolated ADS cells can be transfected with an expression construct encoding a biologically active agent, such as but not limited to at least one of BMP-6 polypeptide, a BMP-6 receptor polypeptide, or a functional fragment thereof. The expression construct can comprise a regulatable promoter operatively linked to at least one coding sequence. The expression vector encoding a biologically active agent (such as but not limited to a BMP-6 polypeptide or a functional fragment thereof) can be administered in addition to the differentiated cell. The expression vector can be selected from the group including but not limited to a viral vector, an adenovirus vector, an adeno-associated virus vector, a plasmid, and a deoxyribonucleic acid molecule.

The ADS cell can be present in or on a biocompatible scaffold. The biologically active agent, such as but not limited to a BMP-6 polypeptide or functional fragment thereof, can be incorporated into the scaffold for controlled release over time.

The ADS cell can be exposed in culture to at least one other biologically active agent, such as but not limited to a growth factor or cytokine. Representative growth factors or cytokines including but not limited a TGF-β superfamily member, an IGF-1, an FGF, an EGF, a PDGF, a parathyroid hormone related peptide (PTHrP), an interleukin, and combinations thereof.

Another cell type other than the ADS cell can be administered along with the ADS cell. The other cell type can be selected from the group including but not limited to a chondrocyte, a fibroblast, an osteoblast, a myoblast, a neuron, a progenitor cell, and combinations thereof.

A subpopulation of differentiated ADS cells can be selected. The subpopulation of differentiated ADS cells can be selected based on: (i) expression of at least one cell surface marker can be selected from the group including but not limited to CD10, CD13, CD31, CD34, CD36, CD44, CD49, CD54, CD55, CD59, CD65 CD105, and CD166; (ii) differential expression of aldehyde dehydrogenase (ALDH); (iii) differential expression of collagen 1; (iv) efflux of a dye such or a nucleic acid label; (v) telomere length or the expression of telomerase; (vi) expression of TGF-β superfamily members; (vii) expression of TGF-β superfamily member receptor polypeptides; or (viii) combinations of any of the foregoing. The dye can comprise Hoechst 33342. The subpopulation of differentiated ADS cells can be selected by repeated passage in culture.

The differentiated ADS cell can be identified as a cell suitable for use in therapeutic restorative and regenerative techniques when gene expression measurements, protein measurements, or combinations thereof meet predetermined parameters.

The ADS cell can be passaged at least twice in culture, wherein the passaging enhances an ability of the cell to express at least one macromolecule associated with a predetermined connective tissue upon exposure to a biologically active agent, such as but not limited to BMP-6 or a functional fragment thereof.

Also disclosed is a joint resurfacing implant adapted for use with a predetermined joint. In some embodiments, the implant comprises a biocompatible scaffold, wherein the scaffold can resurface at least a portion of an articulating surface of the predetermined joint upon implantation. In some embodiments, the implant comprises: a scaffold comprising a biocompatible material; and one or more cells, wherein the scaffold and one or more cells can resurface at least a portion of an articulating surface of a predetermined joint upon implantation. In some embodiments, the implant comprises a cell-seeded biocompatible scaffold, wherein at least a fraction of the cells or scaffold is devitalized before implantation, and wherein the scaffold can resurface at least a portion of an articulating surface of the predetermined joint upon implantation. Methods for making and using the implants in joint resurfacing are also disclosed.

The biocompatible material can comprise a material selected from the group including but not limited to an absorbable material, a non-absorbable material, and combinations thereof. The non-absorbable material can be selected from the group including but not limited to a polytetrafluoroethylene (PTFE), an expanded PTFE (ePTFE), a polyamide, a nylon, a polysulfone, a cellulosic, an acrylic, tantalum, polyvinyl alcohol, carbon, ceramic, a metal, an acrylic, a polycarbonate, a polyester, a polyether, a poly (ether ketone), a poly(ether ether ketone), a poly(aryl ether ketone), a poly(ether ether ketone ether ketone), a poly (ethylene terephthalate), a poly(methyl (meth)acrylate), a polyolefin, a polysulfone, a polyurethane, a polyethylene, a polypropylene, a poly(vinyl chloride), a carbon fiber reinforced composite, a glass fiber reinforced composite, and combinations thereof. The absorbable material can be selected from the group including but not limited to a polyglycolic acid (PGA), a polylactic acid (PLA), a polyglycolide-lactide, a polycaprolactone, a polydioxanone, a polyoxalate, a polyanhydride, a poly(phosphoester), catgut suture, collagen, silk, alginate, agarose, chitin, chitosan, hydroxyapatite, bioabsorbable calcium phosphate, hyaluronic acid, elastin, a polyorthoester, a poly(amino acid), a pluronic/F-12, a poly(ethylene oxide)/poly(ethylene glycol) (PEO/PEG), collagen, gelatin, a blood derivative, plasma, synovial fluid, serum, fibrin, hyaluronic acid, a proteoglycan, elastin, and combinations thereof.

The scaffold can comprise biocompatible fibers. The fibers can comprise a monofilament fiber, a multifilament fiber, a hollow fiber, a fiber having a variable cross-section along its length, or a combination thereof. A two-dimensional fiber scaffold can be utilized, comprising any woven, non-woven, knitted, or braided fiber system. A three-dimensional fiber scaffold can be utilized, comprising three orthogonally woven fiber systems, a plurality of braided fiber systems, a plurality of circular woven fiber systems, or combinations thereof.

The scaffold can comprise a three-dimensional fiber scaffold, the scaffold comprising at least three systems of fibers, wherein (i) two of the three fiber systems define an upper layer, a lower layer, and a medial layer between the upper layer and the lower layer within the three-dimensional fiber scaffold; (ii) one of the at least three fiber systems interconnects the upper layer, the lower layer and the medial layer; and (iii) the at least three fiber systems each comprise a biocompatible material. The at least three fiber systems in at least one of the upper, medial, and lower layers can define a plurality of interstices within the fiber scaffold. The interstices can comprise a pore size ranging from about 1 µm to about 1,000 µm, optionally about 10 µm to about 500 µm, optionally from about 25 µm to about 250 µm, or optionally, from about 50 µm to about 125 µm.

The implant can comprise a shape that corresponds to a majority of an articulating surface of the predetermined joint. The shape can be substantially that of the native predetermined joint.

One or more surfaces of the scaffold can be coated with a biomaterial layer. The biomaterial layer can comprise a gel.

In some embodiments of the scaffold, the one or more cells can be selected from the group including but not limited to primary cells, undifferentiated progenitor cells, stem cells, and combinations thereof. The undifferentiated progenitor cells or stem cells can be selected from the group including but not limited to stem or progenitor cells derived from adipose tissue, bone marrow, synovium, muscle, bone, cord blood, embryos, amniotic fluid, periosteum, and combinations thereof. The primary cells can include but are not limited to chondrocytes, osteoblasts, fibroblasts, fibrochondrocytes, and combinations thereof.

The implant can comprise a biologically active material. The biologically active material can be selected from the group including but not limited to a growth factor, a cytokine, a chemokine, a collagen, gelatin, laminin, fibronectin, thrombin, lipids, cartilage oligomeric protein (COMP), thrombospondin, fibrin, fibrinogen, Matrix-GLA (glycine-leucine-alanine) protein, chondrocalcin, tenascin, a mineral, an RGD (Arginine-Glycine-Aspartic Acid) peptide or RGD-peptide containing molecule, elastin, hyaluronic acid, a glycosaminoglycan, a proteoglycan, water, an electrolyte solution, and combinations thereof.

The predetermined joint can include but is not limited to a hip joint, a knee joint, a shoulder joint, an ankle joint, thumb joint, finger joint, wrist joint, neck joint, spine joint, toe joint, temporomandibular joint, patella, and an elbow joint.

The joint resurfacing implant can be maintained in a bioreactor prior to implantation for a time sufficient to provide tissue that can resurface at least a portion of an articulating surface of the predetermined joint.

In administering the implant, part or all tissues present at site of the joint can be removed. The tissue to be removed can include but is not limited to cartilage, bone, ligaments, meniscus, synovium, and combinations thereof. An entire articulating surface of the joint can be resurfaced. At least a portion of one or more, two or more, etc., articulating surfaces of the joint can be resurfaced in part or in all. At least a portion of all articulating surfaces of the joint can be resurfaced. All articulating surfaces of the joint can be resurfaced.

Accordingly, it is an object of the presently disclosed subject matter to provide novel tissue engineering methods and compositions. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following Description, Drawings, and non-limiting Examples.

BRIEF DESCRIPTION OF THE DRAWINGS

FIGS. 7A-7C demonstrate that three conditions (TGF-β1+Dex, TGF-β3+IGF-1+BMP-6, and BMP-6 only, respectively) showed increased type I collagen staining over other conditions. FIGS. 7D-7F demonstrate that type X collagen expression decreases with BMP-6 with BMP-6 only having the least expression. FIGS. 7G-7I demonstrate that all conditions showed increased type II collagen staining over control, but those with BMP-6 also have strongly staining matrix. FIGS. 7J-7L demonstrate that only those conditions with BMP-6 showed significant staining of chondroitin sulfate with 3B3 antibody.

DETAILED DESCRIPTION

Figure 1:
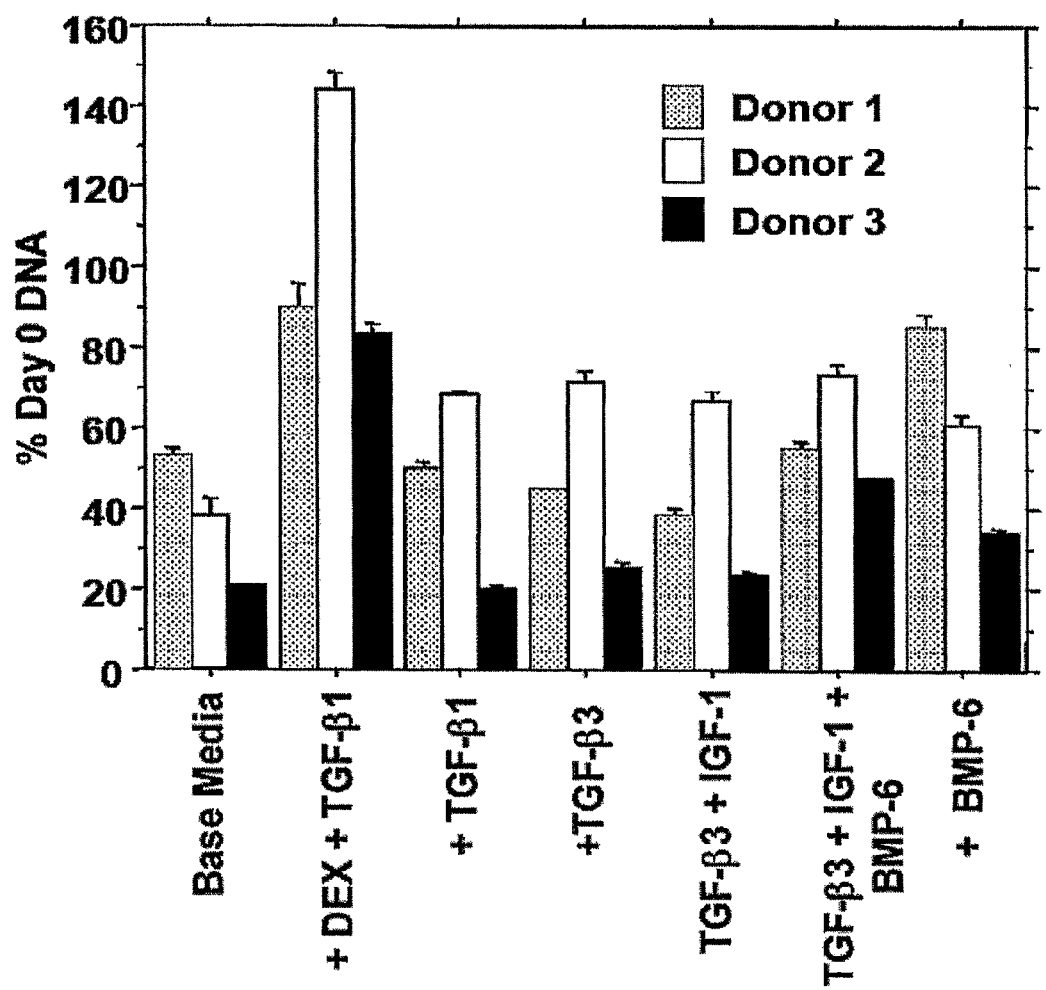
FIG. 1 presents a bar graph of analyses of DNA content after 7 days in culture (n≥4/condition/donor). Data are expressed as mean percent of day 0 DNA±S.E.M. Patterned bars represent donor 1, white bars represent donor 2, and black bars represent donor 3.

The presently disclosed subject matter provides methods and compositions for treating tissue pathologies in a subject, and methods for making the compositions. In some embodiments an implantable composition comprising one or more cells that can develop into one or more tissues at a predetermined site for treatment in the subject is provided. Treatment can be accomplished by implanting the composition at the predetermined site.

In some embodiments, the predetermined tissue types include but are not limited to bone and cartilage, muscle and tendon, and ligament and bone. In some embodiments the predetermined site comprises the resurfacing of the articulating surface in a joint. In any of the presently disclosed embodiments, the sites for the intended replacement tissue can replace multiple tissue types with one implantation (e.g. one tissue replacement to replace bone, cartilage, and the interface of bone and cartilage).

In some embodiments the tissue pathology can comprise a compromise in the normal homeostasis of the tissue, optionally culminating in degeneration of the tissue. The tissue pathology can comprise loss, damage, degeneration, injury, or combinations thereof to the tissue. The treatment can comprise tissue remodeling, repair, regrowth, replacement, regeneration, or combinations thereof.

In some embodiments, the predetermined site comprises a target tissue selected from the group including but not to limited articular cartilage, non-articular cartilage, auricular cartilage, tracheal cartilage, laryngeal cartilage, nasal cartilage, growth plate cartilage, meniscus, labrum, and intervertebral disc. Representative tissue types at the predetermined site also include but are not limited to musculoskeletal or dental connective tissues selected from the group including but not limited to tendon, ligament, periodontal ligament, fascia, and muscle.

In some embodiments, the treatment is solely focused on the treatment of the articular surface of a joint.

To produce the desired implants, the compositions of the presently disclosed subject matter can be maintained under conditions suitable for them to expand and divide to form the desired structures. In some applications, this is accomplished by transferring the compositions to a subject (i.e., in vivo) typically at a site at which the new matter is desired. Thus, for example, the presently disclosed subject matter can facilitate the regeneration of tissues within an animal where the compositions are implanted into such tissues. In other embodiments, the compositions can be prepared in vitro. For examples cells present in the compositions can be induced to differentiate and expand into tissues in vitro. In such applications, the cells can be cultured on substrates or scaffolds that facilitate formation into three-dimensional structures conducive for tissue formation.

I. DEFINITIONS

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law tradition, the terms "a", "an", and "the" are meant to refer to one or more as used herein, including the claims. For example, the phrase "a cell" can refer to one or more cells.

The term "absorbable" is meant to refer to a material that tends to be absorbed by a biological system into which it is implanted. Representative absorbable fiber materials include, but are not limited to polyglycolic acid (PGA), polylactic acid (PLA), polyglycolide-lactide, polycaprolactone, polydioxanone, polyoxalate, a polyanhydride, a poly (phosphoester), catgut suture, collagen, silk, chitin, chitosan, hydroxyapatite, bioabsorbable calcium phosphate, hyaluronic acid, and any other medically acceptable yet absorbable fiber. Other absorbable materials include collagen, gelatin, a blood derivative, plasma, synovial fluid, serum, fibrin, hyaluronic acid, a proteoglycan, elastin, and combinations thereof.

The term "non-absorbable" is meant to refer to a material that tends not to be absorbed by a biological system into which it is implanted. Representative non-absorbable fiber materials include but are not limited to polypropylene, polyester, polytetrafluoroethylene (PTFE) such as that sold under the registered trademark TEFLON® (E.I. DuPont de Nemours & Co., Wilmington, Del., United States of America), expanded PTFE (ePTFE), polyethylene, polyurethane, polyamide, nylon, polyetheretherketone (PEEK), polysulfone, a cellulosic, fiberglass, an acrylic, tantalum, polyvinyl alcohol, carbon, ceramic, a metal (e.g., titanium, stainless steel), and any other medically acceptable yet non-absorbable fiber.

As used herein, the phrases "adipose-derived stem cell" and "ADS cell" refer to a cell with, at a minimum, unipotent potential that can be isolated from adipose tissue and that can be differentiated along various mesodermal and ectodermal lineages. Representative conditions are disclosed herein and have been described in the art, such as in U.S. Pat. No. 6,777,231 or Zuk et al. (2002) Mol Biol Cell 13:4279-4295, the entire contents of each of which are incorporated herein by reference. Adipose-derived stem cells can be isolated using techniques described in these references. In some embodiments, an ADS cell can be isolated from a subject by removing subcutaneous fat from the subject, for example by liposuction. In some embodiments, an adipose-derived stem cell is isolated from a human, in which case it is referred to herein as a human adipose-derived stem (hADS) cell.

As used herein, the terms "anisotropic", "anisotropy", and grammatical variations thereof, refer to properties of a scaffold and/or fiber system as disclosed herein that can vary along a particular direction. Thus, the fiber and/or scaffold can be stronger and/or stiffer in one direction versus another. In some embodiments, this can be accomplished by changing fibers (such as, but not limited to providing fibers of different materials) in warp versus weft directions, and/or in the Z direction, for example. Thus, anisotropic characteristics parallel native properties of a tissue, and it is desirable to match or approximate one or more native properties of the tissue in the implantable composition.

Thus, strength can be provided in the direction needed and indeed it is possible to restore properties of a tissue almost immediately without necessarily needing for cells to grow into functional tissues. However, in some embodiments cells are provided and the growth into functional tissues is also provided. Further, in some embodiments the scaffold can comprise materials at least some, if not all of which, are absorbable materials, such that degradation of the scaffold occurs over time. Thus, in some embodiments, the scaffold is replaced by tissue over time in the subject.

In some embodiments, the terms "anisotropic", "anisotropy" and grammatical variations thereof, can also include, but is not limited to the provision of more fiber in a predetermined direction. This can thus include a change of diameter in a fiber over a length of the fiber, a change in diameter at each end of the fiber, and/or a change in diameter at any point or section of the fiber; a change in cross-sectional shape of the fiber; a change in density or number of fibers in a volumetric section of the scaffold; and the use of monofilament fibers and/or multifilament fibers in a volumetric section of the scaffold; and can even include the variation in material from fiber system to fiber system and along individual fibers in a volumetric section of the scaffold.

As used herein, the term "bioartificial" can refer to an implantable composition that comprises cells that were isolated, grown, and/or manipulated in vitro, or the progeny of such cells. In some embodiments, a bioartificial joint replacement implant as disclosed herein comprises a three-dimensional fiber scaffold and one or more cells that can develop into tissues functioning substantially as bone, cartilage, both bone and cartilage, or other tissues. In some embodiments, a bioartificial joint replacement implant as disclosed herein comprises a scaffold which is partly or wholly acellular. In some embodiments, a bioartificial joint replacement implant as disclosed herein comprises a scaffold that has been partly or wholly decellularized or devitalized at some point in time after being seeded with cells.

The terms "biocompatible" and "medically acceptable" are used synonymously herein and are meant to refer to a material that is compatible with a biological system, such as that of a subject having a tissue (e.g., a joint) to be repaired, restored, and/or replaced in accordance with the presently disclosed subject matter. Thus, the term "biocompatible" is meant to refer to a material that can be implanted internally in a subject as described herein.

The term "composite material", as used herein, is meant to refer to any material comprising two or more components. One of the components of the material can optionally comprise a matrix for carrying cells, such as a gel matrix or resin.

As used herein, the phrases "biologically active agent" and "biologically active factor" are used interchangeably and can refer to a compound or mixture of compounds that when added to a cell in culture induces the cell to enter differentiation (e.g., differentiate at least one step further along a pathway of differentiation).

As used herein, the term "effective amount" refers to an amount of a biologically active agent sufficient to produce a measurable response (e.g., a biologically relevant response in a cell exposed to the differentiation-inducing agent) in the cell. In some embodiments, an effective amount of a differentiation-inducing agent is an amount sufficient to cause a precursor cell to differentiate in in vitro culture into a cell of a tissue at predetermined site of treatment. It is understood that an "effective amount" can vary depending on various conditions including, but not limited to the stage of differentiation of the precursor cell, the origin of the precursor cell, and the culture conditions.

In some embodiments, an "effective amount" of a "biologically active agent" can be determined by assaying the ability of different amounts of a putative biologically active agent to induce the expression of a gene or genes associated with development of a cell that can be used in providing treatment of a tissue pathology as disclosed herein. For example, expression of the gene products aggrecan (for example, the human aggrecan gene product disclosed as GENBANK® Accession No. P16112, or a functional fragment or variant thereof) and type II collagen (for example, the human aggrecan gene product disclosed as GENBANK® Accession No. NP_001835, or a functional fragment or variant thereof) are associated with chondrogenic differentiation. In some embodiments, a gene expression level of aggrecan and/or type II collagen is measured before and after a given amount biologically active agent is provided to a culture of ADS cells (for example, hADS cells), and the levels are compared to determine if the amount of the biologically active agent provided is an "effective amount". In some embodiments, the expression of other genes are similarly determined, including genes that are not associated with particular cartilaginous tissues including, but not limited to type I collagen and type X collagen.

The term "expression vector" as used herein refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA synthesis, processing, and transport, as well as polypeptide synthesis, transport, and post-translational modification of polypeptides. Additionally, processes that affect protein-protein interactions within the cell can also affect gene expression as defined herein.

The terms "heterologous gene", "heterologous DNA sequence", "heterologous nucleotide sequence", "exogenous nucleic acid molecule", and "exogenous DNA segment", as used herein, refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence.

Thus, the terms refer to a DNA segment that is foreign or heterologous to the cell, or homologous to the cell but in a position within the host cell nucleic acid wherein the element is not ordinarily found. In some embodiments where the heterologous DNA sequence comprises an open reading frame, the heterologous DNA sequence is also referred to as a "transgene", although the term "transgene" is not limited to heterologous DNA sequences that comprise an open reading frame.

The terms "inhomogeneous", "inhomogeneity", "heterogeneous", "heterogeneity", and grammatical variations thereof, are meant to refer to a scaffold and/or fiber as disclosed herein that does not have a homogeneous composition along a given length or in a given volumetric section. In some embodiments, an inhomogeneous tissue engineering construct as disclosed herein comprises a composite material, such as a composite comprising a three dimensional scaffold as disclosed herein, cells that can develop tissues that substantially provide the function of bone, cartilage, other joint tissues, or combinations thereof, and a matrix that supports the cells. In some embodiments, an inhomogeneous scaffold as disclosed herein can comprise one or more component systems that vary in their properties according to a predetermined profile, such as a profile associated with the tissue and/or other location in a subject where the scaffold will be implanted. Thus, it is an aspect of the terms "inhomogeneous", "inhomogeneity", "heterogeneous", "heterogeneity", and grammatical variations thereof to encompass the control of individual materials and properties in a scaffold.

The terms "non-linear", "non-linearity", and grammatical variations thereof, refer to a characteristic provided by a scaffold and/or fiber system as disclosed herein such that the scaffold and/or fiber system can vary in response to a strain. As would be appreciated by one of ordinary skill in the art after review of the present disclosure, the scaffolds and/or fiber systems disclosed herein provide stress/stain profiles that mimic that observed in a target such as predetermined tissue or joint. As such stress/strain responses are typically described with reference to a plot, stress/strain responses can be referred to as "non-linear". Important non-linear properties of most biological tissues are significant differences in the strength, stiffness, and/or other properties associated with the magnitude of strain, as well as significant differences in the strength, stiffness, and/or other properties as measured in tension as compared to those measured in compression but along the same axis or direction.

When used in the context of a promoter, the term "linked" as used herein refers to a physical proximity of promoter elements such that they function together to direct transcription of an operably linked nucleotide sequence.

As used herein, the terms "nucleic acid" and "nucleic acid molecule" mean any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., α-enantiomeric forms of naturally-occurring nucleotides), or a combination of both. Nucleic acids can be either single stranded or double stranded.

The terms "operatively linked" and "operably linked", as used herein, refer to a promoter region that is connected to a nucleotide sequence (for example, a coding sequence or open reading frame) in such a way that the transcription of the nucleotide sequence is controlled and regulated by that promoter region. Similarly, a nucleotide sequence is said to be under the "transcriptional control" of a promoter to which it is operably linked. Techniques for operatively linking a promoter region to a nucleotide sequence are known in the art.

As used herein, the term "polypeptide" means any polymer comprising any of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably. The term "polypeptide" encompasses proteins of all functions, including enzymes.

The term "promoter" or "promoter region" each refers to a nucleotide sequence within a gene that is positioned 5' to a coding sequence of a same gene and functions to direct transcription of the coding sequence. The promoter region comprises a transcriptional start site, and can additionally include one or more transcriptional regulatory elements. In some embodiments, a method of the presently disclosed subject matter employs a promoter that is active in an endoderm-derived tissue. Exemplary such promoters include promoters that are active in the liver, the pancreas, the spleen, the lung, etc.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operably linked gene. For example, cell-type-specific or tissue-specific transcriptional regulatory elements can be added to minimal promoters to create recombinant promoters that direct transcription of an operably linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (Hprt), dihydrofolate reductase (Dhfr; Scharfmann et al. (1991) *Proc Natl Acad Sci USA* 88:4626-4630), adenosine deaminase, phosphoglycerate kinase (Pgk), pyruvate kinase, phosphoglycerate mutase, the β-actin promoter (see e.g., Williams et al. (1993) *J Clin Invest* 92:503-508), and other constitutive promoters known to those of skill in the art. "Tissue-specific" or "cell-type-specific" promoters, on the other hand, direct transcription in some tissues and cell types but are inactive in others.

The terms "replace", "replacement", and grammatical variations thereof, refer to any qualitative or quantitative improvement in a target or predetermined tissue or site of treatment observed upon implantation of a composition as disclosed herein. For example, these terms are not limited to full restoration to a normal healthy function, although these terms can refer to this. Rather, these terms are meant to refer to any level of improvement observed in the tissue or at the site.

The terms "reporter gene" and "marker gene" refer to an exogenous gene encoding a product that is readily observed and/or quantitated. A reporter gene is exogenous in that it originates from a source foreign to an intended host cell or, if from the same source, is modified from its original form. Non-limiting examples of detectable reporter genes that can be operatively linked to a transcriptional regulatory region can be found in Alam and Cook (1990) *Anal Biochem* 188:245-254, and PCT International Publication No. WO 97/47763. Exemplary reporter genes include the lacZ gene (see e.g., Rose and Botstein (1983) *Methods Enzymol* 101: 167-180), Green Fluorescent Protein (GFP; Cubitt et al. (1995) *Trends Biochem Sci* 20:448-455), luciferase, and chloramphenicol acetyl transferase (CAT). Any suitable reporter and detection method can be used, and it will be appreciated by one of skill in the art that no particular choice is essential to or a limitation of the presently disclosed subject matter.

The terms "resin", "matrix", or "gel" are used the art-recognized sense and refer to any natural or synthetic solid, liquid, and/or colloidal material that has characteristics suitable for use in accordance with the presently disclosed subject matter. Representative "resin", "matrix", or "gel" materials thus comprise biocompatible materials. In some embodiments, the "resin", "matrix", or "gel" can occupy the pore space of a fiber scaffold as disclosed herein.

The terms "restore", "restoration", and grammatical variations thereof refer to any qualitative or quantitative improvement in a target or predetermined tissue or and/or site of treatment observed upon implantation of a composition as disclosed herein. Thus, these terms are not limited to full restoration of the tissue and/or site to a normal healthy function, although these terms can refer to this. Rather, these terms are meant to refer to any measurable and/or observable level of improvement in the tissue and/or site.

The terms "resurface", "resurfacing", and grammatical variations thereof refer to any qualitative or quantitative replacement of least the majority of the surface area of the surface of tissue upon implantation of a composition as disclosed herein. These terms can also refer to any desired depth of resurfacing; such as but not limited to a layer of micron thickness, to multiple layers of tissue including multiple tissue types, and/or to replacement of a complete structure that provides a surface at the site of treatment. Thus, these terms are not limited to full replacement of the tissue and/or site, although these terms can refer to this. Rather, these terms are meant to refer to replacement of any fraction of the native tissue beyond what is considered by one skilled in the art as a "focal defect". A representative surface is an articulating surface of a joint.

As used herein, the term "selectable marker" refers to a gene or gene product that confers a growth advantage to a cell that expresses it. For example, a selectable marker can allow a cell that expresses it to grow in the presence of a chemical (e.g., a drug such as G418) that would inhibit the growth of or kill cells that do not express the selectable marker. Selectable marker genes include, but are not limited to antibiotic resistance genes, for example the antibiotic resistance gene confers neomycin resistance (herein referred to as the "neo gene").

The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

The terms "viscoelastic", "viscoelasticity", and grammatical variations thereof, are meant to refer to a characteristic provided by a scaffold and/or fiber system as disclosed herein that can vary with a time and/or rate of loading. It is thus envisioned that appropriately viscoelastic scaffolds and/or fiber systems provide time and/or rate of loading characteristics that match or approximate that observed in the predetermined tissue or site. This characteristic pertains to dissipation of energy, which can be provided by the scaffold itself and/or by the scaffold as a composite with cells growing therein, and can also be accomplished by virtue of the choices of fibers that are included in the scaffold. As a particular example, it can be desirable to provide a scaffold that approximates the viscoelastic properties of cartilage.

All references cited in the specification, including patents, patent application publications, journal articles, and all other references cited herein, are incorporated herein by reference to the extent that they supplement, explain, provide a background for, or teach methodology, techniques, and/or compositions employed herein.

II. CELLS AND REAGENTS

II.A. Representative Cells for Joint Resurfacing

The presently disclosed implantable composition can comprise one or more cells that can develop into a suitable replacement of a target tissue (e.g., bone, cartilage, or both bone and cartilage). Particularly, the one or more cells comprise, or are derived from, a precursor cells, such as but not limited to a stem cell. As used herein, the term "stem cell" refers to any unipotent, multipotent, pluripotent and/or totipotent cell that can be differentiated into a desired lineage. As such, the presently disclosed subject matter can employ stem cells that can be differentiated into a tissue appropriate for replacement of native pathological tissues. Representative stem cells include embryonic stem (ES) cells, embryonic germ (EG) cells (e.g., pluripotent cells derived from primordial germ cells), and somatic stem cells (alternatively referred to herein as "adult stem cells").

In some embodiments, the one or more cells described herein comprise an adult stem cell. Adult stem cells can be derived from various adult tissues including, but not limited to liver, bone marrow, umbilical cord blood, brain, peripheral blood, blood vessels, skeletal muscle, adipose tissue, and skin. Methods for the isolation, culturing, and manipulation of adult stem cells from various sources can be found in U.S. Pat. Nos. 6,242,252 and 6,872,389 (hepatic stem cells); U.S. Pat. No. 6,387,367 (hematopoietic/mesenchymal stem cells); Koqler et al. (2004) *J Exp Med* 200:123-135 (placental cord blood); Williams et al. (1999) *The American Surgeon* 65:22-26 (skeletal muscle); U.S. Pat. No. 6,777,231 (adipose tissue); and Blanpain et al. (2004) *Cell* 118:635-

648 (skin), the entire contents of each of which are hereby incorporated in their entireties.

Representative techniques for deriving, growing, and manipulating ES cells and EG cells are disclosed in the following publications: Evans and Kaufman (1981) *Nature* 292:154-156; Martin (1981) *Proc Natl Acad Sci USA* 78:7634+7638; Robertson (1986) *Trends Genet* 2:9-13; PCT International Patent Application Publications WO 96/22362; WO 97/32033; and WO 98/43679; and U.S. Pat. Nos. 6,200,806; 6,090,622; 5,843,780; 5,690,926; 5,670,372; and 5,453,357; and references therein, all of which are incorporated by reference herein in their entireties.

Thus, the presently disclosed subject matter provides in some embodiments the use of the cells described herein for treatment of joint disease. Currently, there are limited treatment options for osteoarthritis, as one example of joint disease. For advanced degeneration, the only current treatment option is replacement of the joint with artificial materials, which include polymers and metals, which effectively act as an artificial joint. While the joint replacement surgeries alleviate pain and restore some function in many of the patients in the short-term, these joint replacements are not intended for long-term use and often require difficult surgical revisions, potentially leading to significant post-operative complications. Some post-operative complications associated with the use of artificial materials include device related osteopenia, osteolysis, excessive wear of the bearing surfaces of the artificial device, and fracture of the bones supporting the implant. Disclosed herein for the first time are approaches for the complete resurfacing of the diseased articular surface with a bioartificial implant, which avoids the complications associated with the introduction of artificial materials due to the biologic nature of the composition of the implanted structure. Further disclosed herein is the use of progenitor, stem, or primary cells in conjunction with a composition that comprises a medium capable of supporting the growth and differentiation of the cells into functional tissue, but not necessarily recapitulating the native structure of the tissue.

II.B. Adipose Derived Stem (ADS) Cells

The ADS and ADS-derived cells of an aspect of the presently disclosed subject matter are useful in providing a source of differentiated and functional cells for research, transplantation, and development of tissue engineering products for the treatment of mammalian disease and traumatic injury repair. Thus, in some aspects, the presently disclosed subject matter provides methods for differentiating ADS cells comprising culturing the cells in a composition that comprises a medium capable of supporting the growth and differentiation of the cells. The presently disclosed subject matter further provides methods for the introduction of these cells into tissue defect areas in need of repair. In some embodiments the tissue defect areas can be treated by exclusively using the ADS and ADS-derived cells of the presently disclosed subject matter.

As an example of one tissue pathology, there are currently limited treatment options for focal cartilage lesions. One treatment option involves drilling into the subchondral bone and exposing the cartilage tissue to growth factors and other molecular agents from the vascular supply found in the bone in the hope that regeneration of the cartilage lesion occurs. A second technique involves the transfer of "healthy" cartilage from non-load bearing areas to "unhealthy" areas to replace the degenerated cartilage. Thirdly, a cell-based therapy exists that utilizes ex vivo cultured autologous chondrocytes reimplanted at the defect site to regenerate the damaged tissue.

All three of these techniques are marked by varying degrees of success, and accordingly, novel techniques and methodologies are needed for the effective remodeling, repair, regrowth, and/or regeneration of cartilage lesions. The presently disclosed subject matter relates to replacement of damaged cartilage as well as other tissues and has broad applications in the field of tissue engineering and regenerative medicine.

ADS cells provide a readily accessible, abundant source of multipotent progenitor cells for applications in tissue engineering and other cell-based therapies. In particular, the potential use of ADS cells for the remodeling, repair, regrowth, and/or regeneration of cartilage has been explored. However, employing the chondrogenic differentiation techniques currently available in the art only results in a mild chondrogenic phenotype in in vitro culture. On the contrary, disclosed herein for the first time are approaches for the unambiguous and robust differentiation of ADS cells along a lineage appropriate for replacement/regeneration of pathological tissue such as degenerated, injured, or damaged cartilage or other connective tissue, and use of these cells in conjunction with a composition that comprises a medium capable of supporting the growth and differentiation of ADS cells into functional tissue, but not necessarily recapitulating the native structure of the tissue.

Thus, the presently disclosed subject matter provides in some embodiments methods and systems for inducing specific phenotypes in ADS cells for the treatment of various tissue pathologies. In contrast to current technologies that are compromised by difficulties in obtaining appropriate stem cells and in differentiating the stem cells as desired in culture, the presently disclosed subject matter provides methods and systems for promoting ADS cell differentiation at a significantly increased rate over previously known methods.

In some embodiments of the presently disclosed subject matter, methods and systems are provided for inducing differentiation comprising providing to ADS cells in culture an effective amount of a biologically active factor (e.g., BMP-6) or a functional fragment thereof.

In some embodiments of the presently disclosed subject matter, methods and systems are provided for determining whether a cell has differentiated into a desired phenotype. Particularly, because the cells of the presently disclosed subject matter have a specific phenotype, they can be employed in tissue engineering. In this regard, the presently disclosed subject matter provides in some embodiments methods of maintaining the ADS cells under conditions sufficient for them to expand and differentiate to form the desired subject matter.

II.C. Isolation of ADS Cells

ADS cells (e.g., hADS cells) are isolated from a subject or obtained directly from an established cell culture line. The subject can be alive or dead, so long as the ADS cells within the subject are viable. Typically, ADS cells are obtained from living donors, using well-recognized protocols such as surgical or suction lipectomy. Such cells can be isolated from the subject to be treated, or from a subject different from the subject to be treated. In some embodiments, the subject from which the cells are isolated is of a different species than the subject into which the cells are to be transferred. Thus, in some embodiments, the ADS cells can be derived from the adipose tissue of a primate, a higher primate (e.g., baboon or ape), or from human adipose tissue, using the methods described herein.

Thus, in some embodiments, the ADS cells are syngeneic (also referred to herein as "autologous") to the subject into which the ADS cells and/or ADS-derived cells are intended to be placed, and in some embodiments the one or more cells are allogeneic (also referred to herein as "heterologous") to the subject. In those embodiments where the one or more cells are allogeneic or xenogeneic to the subject, the subject can be treated as necessary with immunosuppressant drugs such as cyclosporin, azathioprines, or corticosteroids using well-known techniques. Representative immunosuppressive drugs also include, but are not limited to, basiliximab (SIMULECT®; available from Novartis Pharmaceuticals Corp., East Hanover, N.J., United States of America), daclizumab (ZENAPAX®, available from Hoffmann-La Roche Inc., Nutley, N.J., United States of America), muromonab CD3 (ORTHOCLONE OKT3®, available from Ortho Biotech Products, L.P., Bridgewater, N.J., United States of America) and tacrolimus (PROGRAF®, available from Astellas Pharma US, Inc., Deerfield, Ill., United States of America).

As would be readily understood by one of skill in the art, ADS cells refer to stem cells that originate from adipose tissue and are capable of self-renewal. By "adipose" is meant any fat tissue. ADS cells can be isolated from any source of adipose tissue in the subject, although in some embodiments, the ADS cells are isolated from an adipose depot in the body selected from the group consisting of the subcutaneous abdomen, the thigh, the buttocks, and the infrapatellar fat pad. Adipocytes can be harvested by liposuction on an outpatient basis, a relatively non-invasive procedure with cosmetic effects that are acceptable to the vast majority of patients. It is well documented that adipocytes are a replenishable cell population. Even after surgical removal by liposuction or other procedures, it is common to see a recurrence of adipocytes in an individual over time.

ADS cells can comprise a primary cell culture or an immortalized cell line. While stem cells represent less than 0.01% of the bone marrow's nucleated cell population, there are up to $8.6 \times 10^4$ stem cells per gram of adipose tissue (Sen, et al. (2001) *Journal of Cellular Biochemistry*, 81:312-319). Ex vivo expansion over 2 to 4 weeks yields up to 500 million stem cells from 0.5 kilograms of adipose tissue. These cells can be used immediately or cryopreserved for future autologous or allogeneic applications.

In addition, the isolated ADS cells can be further separated into subpopulations of ADS cells based upon any observable, quantifiable, or other trait of the cells for which a separation technique is available or can be designed. In some embodiments, isolated ADS cells are separated into subpopulations using fluorescence-activated cell sorting (FACS) based on the appearance of one or more of cell surface markers. In some embodiments, the following cell surface markers can be employed for separating ADS cells into subpopulations: CD10, CD13, CD31, CD34, CD36, CD44, CD49, CD54, CD55, CD59, CD65 CD105, and CD166.

In some embodiments, the isolated ADS cells can be separated into subpopulations of ADS cells based on differential expression of various genes. In some embodiments, isolated ADS cells are separated into subpopulations based on differential expression of aldehyde dehydrogenase (ALDH), various members of the TGF-β superfamily, TGF-β superfamily receptor, and/or telomerase activity. In some embodiments, the isolated ADS cells are separated into subpopulations of ADS cells based on telomere length. In some embodiments, the isolated ADS cells can be separated into subpopulations of ADS cells based on efflux of macromolecules including, but not limited to dyes (e.g., Hoechst 33342) or nucleic acid labels. In some embodiments, the isolated ADS cells can be separated into subpopulations of ADS cells based on responsiveness to a particular growth factor (e.g., BMP-6). It is understood that two or more of these separation strategies can be employed together to produce subpopulations of ADS cells either before or after the induction of differentiation.

Such isolated ADS cells and populations can be clonally expanded, if desired, using a suitable method for cloning cell populations. For example, a proliferated population of cells can be physically picked and seeded into a separate plate (or the well of a multi-well plate). Alternatively, the cells can be subcloned onto a multi-well plate at a statistical ratio for facilitating placing a single cell into each well (e.g., from about 0.1 to about 1 cell/well). In some embodiments, the cells can be cloned by plating them at low density (e.g., in a petri-dish or other suitable substrate) and isolating them from other cells using devices such as a cloning rings. Alternatively, where an irradiation source is available, clones can be obtained by permitting the cells to grow into a monolayer and then shielding one and irradiating the rest of cells within the monolayer. The surviving cells then can grow into a clonal population.

II.D. Genetic Manipulation of Cells

In some embodiments, the cells, for example ADS cells, can be genetically modified, e.g., to express exogenous genes or to repress the expression of endogenous genes. In some embodiments, the presently disclosed subject matter provides methods of genetically modifying such cells and populations. In accordance with these methods, the cells can be exposed to an expression construct comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode a biologically active (e.g., functional) fragment of a protein.

Thus, for example, the coding polynucleotide can encode a gene conferring resistance to a toxin, a hormone (such as peptide growth hormones, hormone releasing factors, sex hormones, adrenocorticotrophic hormones, cytokines (e.g., interferins, interleukins, lymphokines), etc.), a cell-surface-bound intracellular signaling moiety (e.g., cell adhesion molecules, hormone receptors, etc.), a factor promoting a given lineage of differentiation, etc. Of course, where it is desired to employ gene transfer technology to deliver a given transgene, the sequence will be known. In some embodiments, the coding polynucleotide encodes a growth factor. In some embodiments, the coding polynucleotide encodes BMP-6 or a functional fragment thereof. In some embodiments, the coding polynucleotide encodes BMP-6 receptor or a functional fragment thereof.

The cells can be stably or transiently transfected or transduced with a nucleic acid of interest using a plasmid, viral or alternative vector strategy. With respect to ADS cells, nucleic acids of interest include, but are not limited to, those encoding gene products which enhance the production of extracellular matrix components found in cartilage; examples include, collagen type II, TGF-β, BMP, activin and insulin-like growth factor.

Thus, in some embodiments, the transduction of regulatory genes into the cells, for example ADS cells, can be performed with viral vectors (adenovirus, retrovirus, adeno-associated virus, or other vector) purified by cesium chloride banding or any other well-known method at a multiplicity of infection (viral units:cell) of between 10:1 to 2000:1. Cells can be exposed to the virus in serum-free or serum-containing medium in the absence or presence of a cationic detergent such as polyethyleneimine or Lipofectamine™ (available from Invitrogen, Carlsbad, Calif., United States of America) for a period of 1 hour to 24 hours (Byk et al. (1998) *Human Gene Therapy* 9:2493-2502; Sommer et al. (1999) *Calcif. Tissue Int.* 64:45-49) or in three dimensional cultures by incorporation of the plasmid DNA vectors directly into a biocompatible polymer (Bonadio et al. (1999) *Nat. Med.* 5:753-759).

In some embodiments, cells, for example ADS cells, are transfected with the gene to be expressed to produce cells having stably incorporated therein the DNA encoding the molecules to be expressed. Stable transfections can be obtained by culturing and selecting for expression of the desired encoded molecules. In some embodiments, the cells that exhibit stable expression can be seeded onto or into the appropriate fiber matrix and implanted in a subject. For the tracking and detection of functional proteins encoded by these genes, the viral or plasmid DNA vectors can contain a readily detectable marker gene, such as the green fluorescent protein (GFP) or β-galactosidase enzyme, both of which can be tracked by histochemical means.

Within the expression cassette, the coding polynucleotide can be operably linked to a suitable promoter. Examples of suitable promoters include prokaryotic promoters and viral promoters (e.g., retroviral inverted terminal repeats (ITRs), long terminal repeats (LTRs), immediate early viral promoters (IEp), such as herpes virus IEp (e.g., ICP4-IEp and ICP0-IEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit β-globin regulatory elements), constitutively active promoters (e.g., the β-actin promoter, etc.), signal specific promoters (e.g., inducible promoters such as a promoter responsive to RU486, etc.), and tissue-specific promoters. It is well within the skill of the art to select a promoter suitable for driving gene expression in a pre-defined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene can be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpes viruses, lentiviruses, papillomaviruses, retroviruses, etc.). Any method of constructing the desired expression cassette within such vectors can be employed, many of which are well known in the art (e.g., direct cloning, homologous recombination, etc.). Of course, the choice of vector will largely determine the method used to introduce the vector into the cells (e.g., by protoplast fusion, calcium-phosphate precipitation, gene gun, electroporation, infection with viral vectors, etc.), which are generally known in the art.

In some embodiments, the genetically altered (e.g., ADS) cells can be employed as bioreactors for producing the product of the transgene. In some embodiments, the genetically modified cells are employed to deliver the transgene and its product to a subject. For example, the cells, once genetically modified, can be introduced into the subject under conditions sufficient for the transgene to be expressed in vivo.

II.E. Induction of Differentiation for Tissue Replacement

Another object of the presently disclosed subject matter is to provide for the identification and study of compounds that enhance the differentiation of ADS cells (e.g., hADS cells) into cells capable of forming an extracellular matrix capable of functioning in place of the native tissue. Representative, non-limiting extracellular matrix proteins are disclosed in the Examples. Compounds that enhance differentiation can be of value in the treatment of partial or full cartilage defects, osteoarthritis, traumatized cartilage, and cosmetic surgery of inborn defects including cleft palate and deviated septum, among other treatments.

After isolation, ADS cells can be cultured in vitro for a time and under conditions sufficient to induce one or more of the cells to undergo differentiation. In some embodiments, one or more biologically active agents are added to the culture medium. In some embodiments, a biologically active agent comprises a BMP-6 polypeptide, or a functional fragment thereof. In some embodiments, a biologically active agent comprises a BMP-6 polypeptide, or a functional fragment thereof, in combination with one or more additional growth factors and/or cytokines. It is understood that for any polypeptides that are employed as constituents of a biologically active agent, it is not necessary that full length polypeptides be employed, as functional fragments can also be used. As used herein, the term "functional fragment" refers to a subsequence of a polypeptide (or a subsequence of a nucleic acid encoding such a polypeptide fragment) that is characterized by at least some activity in differentiation when part of a biologically active agent.

In some embodiments, the method of inducing differentiation in stem cells comprises (a) providing to a stem cell in culture an effective amount of a biologically active factor (e.g., BMP-6) or a functional fragment thereof; and (b) growing the stem cell (e.g. ADS cell) in culture for a time sufficient for differentiation to occur, wherein differentiation is determined to have occurred when at least one stem cell (e.g. ADS cell) exhibits expression of a macromolecule associated with the native, healthy tissue to be replaced (i.e., native extracellular composition of the tissue prior to injury, disease, or degeneration). Representative, non-limiting extracellular matrix proteins are disclosed in the Examples.

In some embodiments, the method further comprises passaging the stem cell (e.g. ADS cell) repeatedly (e.g., at least twice) in culture, wherein the passaging enhances an ability of the cell to express at least one macromolecule associated with the predetermined target tissue upon exposure to a biologically active factor or a functional fragment thereof. Representative macromolecules are disclosed in the Examples.

In some embodiments, the method further comprises providing to the stem cells (e.g. ADS cells) a predetermined effective amount of a second biologically active factor.

Represesentative biologically active factors can be selected from the group including, but not limited to, growth factors, e.g., TGF-β superfamily members (including but not limited to BMP-6, TGF-β1, TGF-β2, TGF-β3), IGF-1, FGF, an EGF, a PDGF, a parathyroid hormone related peptide (PTHrP), an interleukin, cytokines, chemokines, gelatins, laminins, fibronectins, thrombins, lipids, cartilage oligomeric proteins (COMP), thrombospondins, fibrins, fibrinogens, Matrix-GLA protein, chondrocalcin, tenascin, a mineral, an RGD peptide, an RGD-peptide containing molecule, elastin, hyaluronic acid, a glycosaminoglycan, a proteoglycan and other molecules that alone or in combination are capable of inducing the differentiation of an ADS cell into a cell or a cell that is further differentiated along the appropriate target lineage than is the ADS cell. In some embodiments a composition to be administered to cells can consist essentially of a given biologically active agent (such as but not limited BMP-6), and in some embodiments such a composition can consist of a given biologically active agent.

In some embodiments, the biologically active agent is selected from the group including but not limited to parathyroid hormone, a transforming growth factor (e.g., a TGF-α, and/or a TGF-β), an insulin-like growth factor (e.g., IGF-I), a platelet-derived growth factor (PDGF), a fibroblast growth factor (FGF), an epidermal growth factor (EGF), a vascular endothelial growth factor (VEGF), and combinations thereof. In some embodiments, the biologically active agent is a bone morphogenetic protein (BMP), and in some embodiments the BMP is BMP-6 (e.g., human BMP-6). In some embodiments, the human BMP-6 comprises amino acids 374-513 of GEN BANK® Accession No. NP_001709, or a functional fragment or variant thereof, and/or is encoded by a nucleic acid comprising GENBANK® Accession No. NM_001718, or a function fragment or variant thereof.

Further, it is to be understood that in some embodiments, the biologically active agent (e.g., BMP-6) can be incorporated into an implantable composition of the presently disclosed subject matter for controlled release over time.

II.F. Bone Morphogenic Proteins

Bone morphogenetic proteins (BMPs) are characterized by their ability to promote, stimulate or otherwise induce the formation of cartilage and/or bone. Accordingly, members of the BMP family of proteins can be used in compositions to induce bone and/or cartilage formation, wound healing and tissue repair, treatment of bone and/or cartilage defects, periodontal disease and other tooth repair processes, treatment of osteoporosis and increase of neuronal survival.

It has been presently discovered, as discussed herein in detail, that BMP-6 in combination with several growth factors, supplements, and other soluble mediators increases the gene expression and biosynthesis of collagen and proteoglycan by several orders of magnitude as compared to other differentiation protocols that have been previously published. Further, it has also been shown herein that BMP-6 in the absence of other growth factors strongly promotes a robust differentiation towards a generated tissue type which may be used to replace many different tissue types (e.g., ligament, tendon, IVD, meniscus, and cartilage). BMP-6 is a member of a different BMP family subgroup than are BMP-2 and BMP-4, and is thus different from BMP-1, -2, -3, -4, and -5. In some embodiments, the effective amount of BMP-6 ranges from about 1 picogram/mL to about 10 milligram/mL.

II.G. Detection of Differentiation

After culturing the cells in a suitable medium for a suitable time (e.g., several days to a week or more), the cells can be assayed to determine whether, in fact, they have differentiated to acquire physical qualities of a desired cell type. Thus, in some embodiments the presently disclosed subject matter provides methods for testing ADS cell-derived cells.

One measurement of differentiation per se is telomere length, undifferentiated stem cells having longer telomeres than differentiated cells; thus, the cells can be assayed for the level of telomerase activity. Alternatively, RNA or proteins can be extracted from the cells and assayed (via Northern hybridization, rtPCR, Western blot analysis, etc.) for the presence of markers indicative of the desired phenotype.

Thus, methods for determining whether an ADS cell has differentiated into a desired phenotype are also provided. In some embodiments, the methods comprise (a) obtaining mRNA from an ADS cell that has been exposed to a biologically active agent; and (b) determining from the mRNA a level of expression of at least one gene associated with a desired differentiation, wherein the level of expression determined for the at least one gene is indicative of differentiation of the ADS cell. In some embodiments, the methods comprise determining from the ADS cell a level of expression of at least one protein associated with a desired differentiation. In some embodiments, the cells can be assayed immunohistochemically or stained, using tissue-specific stains.

In some embodiments, the methods comprise measuring expression of at least one gene associated with a desired differentiation to determine when at least a subpopulation of the ADS cells have differentiated. In some embodiments, the appearance of an ADS cell-derived phenotype is tested and/or confirmed by testing the ADS cell grown in culture to determine when differentiation has occurred, wherein the testing comprises utilizing a technique for measuring gene expression to determine when the ADS cell has differentiated, and wherein the technique for measuring gene expression comprises measuring a level of expression of at least one gene associated with a desired phenotype. In some embodiments, the at least one gene associated with a desired differentiation is selected from the group consisting of aggrecan, type I collagen, type II collagen, type X collagen, and combinations thereof.

Accordingly, the presently disclosed subject matter provides methods for identifying cells, for example ADS-derived cells, suitable for use in therapeutic applications. In some embodiments, the differentiated ADS cell is identified as suitable for use in therapeutic restorative and regenerative techniques when gene expression measurements, protein measurements, or combinations thereof meet predetermined parameters, such as but not limited to those disclosed in the Examples presented herein.

Other methods of assessing developmental phenotype are known in the art, and any of them are appropriate. For example, the cells can be sorted by size and granularity. Also, the cells can be used to generate monoclonal antibodies, which can then be employed to assess whether they preferentially bind to a given cell type. Correlation of antigenicity can confirm that the stem cell has differentiated along a given developmental pathway.

II.H. Administration of Cells to Subjects

As is known in the art, when the cells are to be administered to a subject, it is preferable that the cell culture medium be biologically compatible with the subject. Stated another way, in some embodiments the cell culture medium that is used to culture and induce cells does not contain any components that would be expected to negatively affect the health of the subject after administration of the induced cells. Thus, an appropriate cell culture medium can also comprise one or more serum-free medium supplements. As used herein, the term "serum-free medium supplement" refers to a supplement that can be added to a medium to replace some or all of the serum that would normally be added to the medium to support the propagation and/or maintenance of cells in culture.

Serum-free medium supplements typically comprise about 10-25 mM HEPES, about 1-4 grams per liter (g/L) sodium bicarbonate, up to about 5 micrograms per liter (μg/L) hypoxanthine, up to about 10 μg/L thymidine, up to about 1.5 g/L sodium pyruvate, up to about 2.0 g/L L-glutamine, and up to about 30 µg/L phenol red. Various trace elements and other growth factors can also be added to serum-free medium supplements. An exemplary serum-free medium supplement is OPTI-MEM® I reduced serum medium supplement, sold by Invitrogen Corp. (Carlsbad, Calif., United States of America) in powder and liquid forms (Catalog Nos. 22600-050, 22600-134, 11058-021, 31985-062, 31985-070, 31985-088, and 51985-034). Other serum-free medium supplements include BIOGRO-1 and BIO-GRO-2 (Biological Industries Ltd., Kibbutz Beit Haemek, Israel) and the Nutridoma family of serum free medium supplements sold by Roche Applied Science (Indianapolis, Ind., United States of America).

For analysis and/or administration into a subject, the induced cells can be treated with trypsin/EDTA in order to form a single cell suspension and resuspended in an appropriate pharmaceutically acceptable carrier such as phosphate-buffered saline. Representative carriers include, but are not limited to, calcium alginate, agarose, types I, II, IV or other collagen isoform, fibrin, poly-lactic/poly-glycolic acid, hyaluronate derivatives or other materials (Perka et al. (2000) $J.$ Biomed. Mater. Res. 49:305 311; Sechriest et al. (2000) $J.$ Biomed. Mater. Res. 49:534 541; Chu et al. (1995) $J.$ Biomed. Mater. Res. 29:1147 1154; Hendrickson et al. (1994) Orthop. Res. 12:485 497). Thus, in some embodiments, the induced cells can be transplanted into a desired site in a subject (i.e., a joint) to promote in situ repair or regeneration of cartilage, bone, or cartilage and bone. In some embodiments, two different types of cells are administered, for example, another cell type is administered along with a progenitor, stem, or primary cell. The other cell type can be selected from the group consisting of, but not limited to, a chondrocyte, a fibroblast, an osteoblast, a myoblast, a neuron, a progenitor cell, and combinations thereof.

Thus, in some embodiments the cells can be administered to a target tissue selected from the group consisting of, but not limited to, articular cartilage, non-articular cartilage, auricular cartilage, tracheal cartilage, laryngeal cartilage, nasal cartilage, growth plate cartilage, meniscus, labrum, and intervertebral disc. In some embodiments, the target tissue can comprise a musculoskeletal or dental connective tissue selected from the group consisting of, but not limited to, a tendon, ligament, periodontal ligament, fascia, and muscle. It is to be understood that the target tissue can comprise multiple tissue types that are integrated with one another, selected from the group consisting of, but not limited to, bone and cartilage (e.g., an osteochondral junction), muscle and tendon (e.g., a myotendinous junction), and ligament and bone (e.g., an insertion site).

In some embodiments, the target tissue is the surface of an articulating joint It is to be understood that the target tissue can comprise multiple tissue types that are integrated with one another, selected from the group consisting of, but not limited to, bone and cartilage (e.g., an osteochondral junction), muscle and tendon (e.g., a myotendinous junction), and ligament and bone (e.g., an insertion site).

In some embodiments, the one or more cells to be administered to a subject are present in a matrix (e.g., a gel) within the pores of a fiber scaffold. The fiber scaffold can be used as a substrate to facilitate the growth and/or differentiation of cells. Thus, in some embodiments, the cells can be used to grow pieces of functional cartilage and/or bone in vitro for implantation into a desired site in the patient (e.g., site of pathology or joint surface).

III. SCAFFOLDS FOR IMPLANTABLE COMPOSITIONS

The presently disclosed subject matter provides in some embodiments implantable compositions comprising scaffolds for use at a predetermined site in a subject. In some embodiments the presently disclosed subject matter provides a joint replacement or resurfacing implant (for example, an implant that is intended to cover the majority of the articulating surface or surfaces of a joint) adapted for use with a predetermined joint that combines novel composite biomaterials with or without cells to produce a composite implant comprising cells that differentiate into, and/or have differentiated to, tissues capable of substantial bone and/or cartilage function, among other functions. In contrast to current technologies that seek to repair small pieces of cartilage or focal defects in a predetermined joint, a joint replacement implant of the presently disclosed subject matter is used in some embodiments to resurface the majority or entirety of surfaces of damaged or diseased joints.

A representative joint addressed in some embodiments of the presently disclosed subject matter is the hip, due to the high incidence of hip osteoarthritis. In some embodiments of the presently disclosed subject matter, a joint replacement implant is engineered into a hemispherical shape for use in a hip replacement. In some embodiments, the joint replacement implant is grown using human adult stem, other progenitor, and or primary cells seeded onto three-dimensional woven composite biomaterial matrices that provide desired biomechanical properties. A combination of growth modulating materials as defined herein and physical stimuli can be used within a bioreactor to promote differentiation of integrated bone and cartilage within the joint replacement implant. This approach can be used to fabricate implants, which can provide substantial cartilage or cartilage/bone function for replacement of the surfaces of the joint (e.g., femoral head and/or acetabular cup), shoulder, knee, finger (e.g., thumb, phalanges, carpo-metacarpal, trapeziometacarpal), temporomandibular joint, patella, elbow, ankle, or any other diarthrodial joints.

Figure 8:
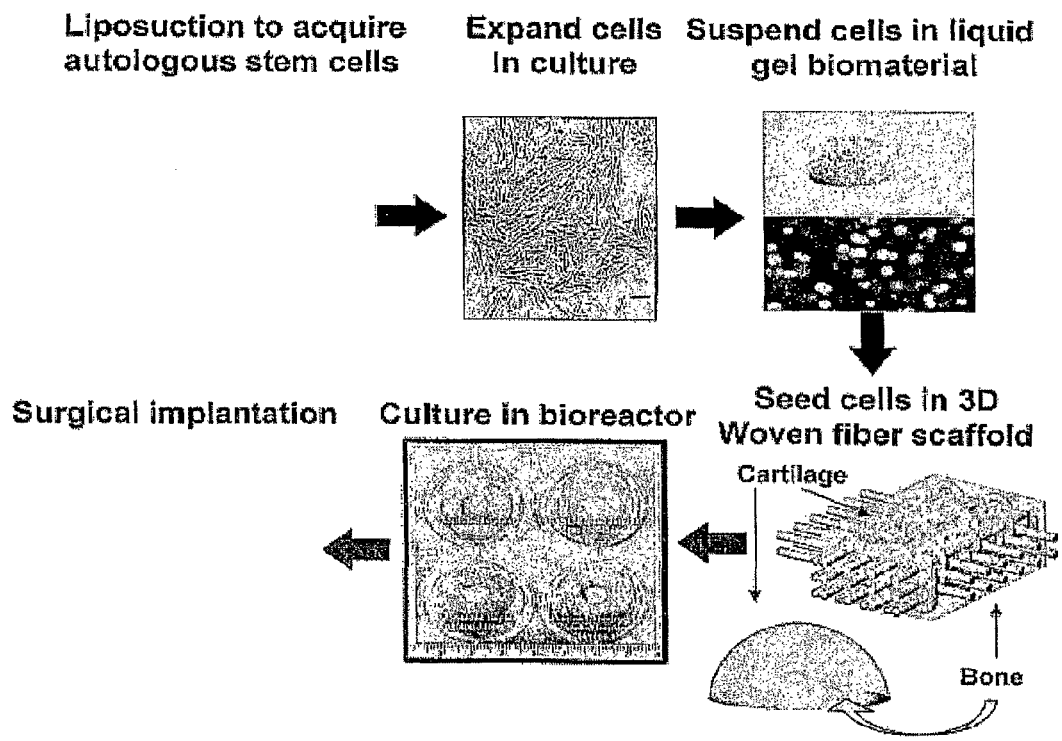
FIG. 8 is a diagram of the steps of one embodiment of the presently disclosed subject matter, involving the formation of a bioartificial hip implant from autologous stem cells.

A representative, non-limiting process that can be employed to form an exemplary joint replacement implant, a bioartificial hip, is schematically depicted in FIG. 8. As shown in FIG. 8, liposuction can be employed to isolate autologous (or heterologous) stem cells (including but not limited to adipose-derived stem cells), which can then be expanded in culture. Once a sufficient number of such stem cells are produced, the cells can be concentrated and suspended in a matrix such as a gel biomaterial and applied to a three-dimensional scaffold, which is then placed in culture or in a bioreactor until sufficient growth and/or differentiation has occurred so that the resulting joint replacement implant can be implanted into the subject.

Thus, the presently disclosed subject matter represents a significant departure from previous approaches in that a living tissue substitute for the entire joint surface is provided, rather than a repair of an isolated defect. Since the joint replacement implant comprises living tissue, it can integrate with the subject's tissues and can require significantly less invasive surgery and minimal removal of native tissues. In some embodiments, a joint replacement implant is provided that can be implanted using minimally invasive surgery as a temporary replacement for an osteoarthritic hip or other joint surfaces. In such embodiments, standard prosthetic joint replacement surgery can be delayed significantly, such as by 5-10 years or longer. This can be of interest in to certain subjects, including younger and/or active subjects.

III.A. Fibers

Disclosed herein, in some embodiments, are joint replacement implants comprising a fiber scaffold. Two-dimensional or three-dimensional fiber scaffolds can be employed. These scaffolds can comprise systems of fibers, wherein, for example for a three-dimensional fiber system, two of the three fiber systems define an upper layer, a lower layer, and a medial layer between the upper layer and the lower layer within the three-dimensional fiber scaffold, and wherein one of the at least three fiber systems interconnects the upper layer, the lower layer, and the medial layer. The at least three fiber systems can each comprise a biocompatible material, and the biocompatible material can comprise an absorbable material, a non-absorbable material, or combinations thereof.

Fibers can be monofilament, multifilament, or a combination thereof, and can be of any shape or cross-section including, but not limited to bracket-shaped (i.e., [), polygonal, square, I-beam, inverted T shaped, or other suitable shape or cross-section. The cross-section can vary along the length of fiber. Fibers can also be hollow to serve as a carrier for macromolecules (e.g., antibiotics, growth factors, etc.), cells, and/or other materials as described herein. In some embodiments, the fibers can serve as a degradable or non-degradable carriers to deliver a specific sequence of growth factors, antibiotics, or cytokines, etc., embedded within the fiber material, attached to the fiber surface, or carried within a hollow fiber.

Fiber diameters can be of any suitable length in accordance with characteristics of the target or predetermined tissue in or at which the implant is to be placed. Representative size ranges include a diameter of about 1 micron, about 5 microns, about 10 microns about 20 microns, about 40 microns, about 60 microns, about 80 microns, about 100 microns, about 120 microns, about 140 microns, about 160 microns, about 180 microns, about 200 microns, about 220 microns, about 240 microns, about 260 microns, about 280 microns, about 300 microns, about 320 microns, about 340 microns, about 360 microns, about 380 microns, about 400 microns, about 450 microns or about 500 microns (including intermediate lengths). In various embodiments, the diameter of the fibers can be less than about 1 micron or greater than about 500 microns. Additionally, nanofibers fibers with diameters in the nanometer range (1-1000 nanometers) are envisioned for certain embodiments. Additionally, large fibers with diameters up to 3.5 cm are envisioned for certain embodiments.

In some embodiments, representative fiber size ranges include 25 μm to 100 μm in diameter. As would be apparent to one in ordinary skill in the art upon review of the present disclosure, 25 μm comprises approximately the size of a microsurgery suture. In some embodiments the diameter of the fibers provides just enough integrity for the fiber to be held under tension and therefore implemented in a process of making as disclosed herein.

In some embodiments, the distance between the fibers can range from about 1 micron to about 1,000 microns. For example, the distance between the fibers can be about 5 microns, about 10 microns, about 50 microns, about 70 microns, about 90 microns, about 100 microns, about 120 microns, about 140 microns, about 160 microns, about 180 microns, about 200 microns, about 220 microns, about 240 microns, about 260 microns, about 280 microns, about 300 microns, about 320 microns, about 340 microns, about 360 microns, about 380 microns, about 400 microns, about 450 microns or about 500 microns. In various embodiments the distance between the fibers can be less than 1 micron or greater than 500 microns.

In other embodiments of the presently disclosed subject matter, the fibers or subset of fibers, can contain one or more therapeutic agents such that the concentration of the therapeutic agent or agents varies along the longitudinal axis of the fibers or subset of fibers. The concentration of the active agent or agents can vary linearly, exponentially or in any desired fashion, as a function of distance along the longitudinal axis of a fiber. The variation can be monodirectional; that is, the content of one or more therapeutic agents can decrease from the first end of the fibers or subset of the fibers to the second end of the fibers or subset of the fibers. The content can also vary in a bidirectional fashion; that is, the content of the therapeutic agent or agents can increase from the first ends of the fibers or subset of the fibers to a maximum and then decrease towards the second ends of the fibers or subset of the fibers.

Thus, in some embodiments, the fibers serve as a degradable or nondegradable carrier to deliver one or more specific sequences of growth factors, antibiotics, cytokines, etc. that are embedded within the fiber matter, attached to the fiber surface, or carried within a hollow fiber.

For fibers that contain one or more therapeutic agents, the agent or agents can include: a growth factor, an immunodulator, a compound that promotes angiogenesis, a compound that inhibits angiogenesis, an anti-inflammatory compound, an antibiotic, a cytokine, an anti-coagulation agent, a pro-coagulation agent, a chemotactic agent, agents that promotes apoptosis, an agent that inhibits apoptosis, a mitogenic agent, a radioactive agent, a contrast agent for imaging studies, a viral vector, a polynucleotide, therapeutic genes, DNA, RNA, a polypeptide, a glycosaminoglycan, a carbohydrate, a glycoprotein, and combinations thereof.

In some embodiments, the three-dimensional fiber scaffold comprises a 3-D textile scaffold. In this case, the fiber systems are referred to as yarn systems.

Fiber scaffolds suitable for inclusion with the presently disclosed subject matter can be derived from any suitable source (e.g., matrigel), or any of a variety of commercial sources for suitable fiber scaffolds (e.g., polyglycolic acid can be obtained from sources such as Ethicon, Somerville, N.J., United States of America).

In some embodiments, the fiber scaffold can be prepared in a hydrated form or it can be dried or lyophilized into a substantially anhydrous form or a powder. Thereafter, the powder can be rehydrated for use as a cell culture substrate, for example by suspending it in a suitable cell culture medium. In this regard, the fiber scaffold can be mixed with other suitable scaffold materials, such as described above.

In some embodiments, the fiber scaffold is biodegradable over time, such that it will be absorbed into the subject as it develops. Suitable fiber scaffolds, thus, can be formed from monomers such as glycolic acid, lactic acid, propyl fumarate, caprolactone, hyaluronan, hyaluronic acid, and the like. Other fiber scaffolds can include proteins, polysaccharides, polyhydroxy acids, polyorthoesthers, polyanhydrides, polyphosazenes, or synthetic polymers (particularly biodegradable polymers). In some embodiments, suitable polymers for forming the fiber scaffold can include more than one monomer (e.g., combinations of the indicated monomers). Further, the fiber scaffold can include hormones, such as growth factors, cytokines, and morphogens (e.g., retinoic acid, arachidonic acid, etc.), desired extracellular matrix molecules (e.g., fibronectin, laminin, collagen, etc.), or other materials (e.g., DNA, viruses, other cell types, etc.) as desired.

Polymers for use in the presently disclosed subject matter include single polymer, co-polymer or a blend of polymers of poly(L-lactic acid), poly(DL-lactic acid), polycaprolactone, poly(glycolic acid) or polyanhydride. Naturally occurring polymers can also be used such as reconstituted or natural collagens or silks. Those of skill in the art will understand that these polymers are just examples of a class of biodegradable polymer matrices that can be used in the presently disclosed subject matter. Further biodegradable matrices include polyanhydrides, polyorthoesters, and poly (amino acids). Any such matrix can be utilized to fabricate a biodegradable polymer matrix with controlled properties for use in the presently disclosed subject matter.

Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers can include, for example, proteins, such as albumin.

Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, polyethylenes (such as, for example, polyethylene glycol (including the class of compounds referred to as PLURONICS®, commercially available from BASF, Parsippany, N.J., U.S.A.), polyoxyethylene, and polyethylene terephthlate), polypropylenes (such as, for example, polypropylene glycol), polyurethanes, polyvinyl alcohol (PVA), polyvinyl chloride and polyvinylpyrrolidone, polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof.

The polymeric materials can be selected from those materials which can be polymerized or their viscosity altered by application of exogenous means. For example, by application of light, ultrasound, radiation, or chelation, alone or in the presence of added catalyst, or by endogenous means, for example, a change to physiological pH, diffusion of calcium ions (alginate) or borate ions (polyvinyl alcohol) into the polymer, or change in temperature.

It is also to be understood that while in some embodiments, the one or more cells of the presently disclosed subject matter can be employed in conjunction with the fibers of the 3-D fiber scaffold, it is also envisioned that the one or more cells can be present in a matrix comprising a gel or polymer phase without a fiber scaffold. Further, it is to be understood that in some embodiments, the differentiation-promoting factor (e.g., BMP-6) can be incorporated into the 3-D fiber scaffold for controlled release over time.

III.B. Three-Dimensional Weaving

In some embodiments, the presently disclosed subject matter provides a novel 3-D weaving technology that can be employed to form composite anatomically-shaped biomaterial scaffolds that can be impregnated with a gelatinous material (fibrin, gelatin, alginate, agarose, etc.) to promote cell growth. The fiber-reinforced scaffold can be woven to reproduce the biomechanical properties of both cartilage and bone and can be coated with biologically active factors in a site-specific manner to promote cell differentiation, growth, and activity as required. One representative form of the scaffold is a largely hemispherical two-phase (bone/cartilage) construct. Other embodiments can include a "saddle" shaped two-phase (bone/cartilage) construct. Other shapes can be made to mimic more complex joint architecture including, but not limited to, the knee joint, with multiple tissues (bone/cartilage/meniscus).

An advantage of presently disclosed weaving technology is that the large, ordered, and interconnected pores or interstices of the 3-D weave allow for consistent and even distribution of cells (including but not limited to ADS or ADS-derived cells) throughout the composite scaffold. The interstices comprise a pore size ranging in some embodiments about 1 µm to about 1,000 µm, in some embodiments about 5 µm to about 750 µm, in some embodiments from about 10 µm to about 500 µm, in some embodiments from about 25 µm to about 250 µm, and in some embodiments from about 50 µm to about 125 µm. Such a structure provides sufficient area onto which the cells can grow and proliferate.

Three-dimensional fiber scaffolds are produced in some embodiments using a 3-D weaving loom, specifically constructed to produce precise structures from fine diameter fibers. A computer controlled weaving machine can produce true 3-D shapes by placing fibers axially (x-warp direction), transversely (y-weft, or filling direction), and vertically (z-thickness direction). Multiple layers of warp yarns are separated from each other at distances that allow the insertion of the weft layers between them. Two layers of Z-yarns, which are normally arranged in the warp direction, are moved (after the weft insertion) up and down, in directions opposite to the other. This action is followed by the "beat-up", or packing of the weft into the scaffold, and locks the two planar fibers (the warp and weft) together into a uniform configuration. Change of yarn densities can be achieved for warp by altering the reed density and warp arrangement and for weft by varying the computer program controlling the take-up speed of a stepper motor.

In some embodiments, the three-dimensional fiber scaffold comprises three orthogonally woven fiber systems, a plurality of braided fiber systems, a plurality of circular woven fiber systems, or combinations thereof.

In some embodiments the presently disclosed subject matter comprises a 3-D weave of fibers in three orthogonal directions. In comparison to standard weaving methods, this process eliminates fiber crimp and forms a true 3-D structure. In general, most current 3-D textile composites are constructed by laminating multiple 2-D structures together, and the lamination interface between multiple layers is the weak point in the composite where debonding or delamination can always occur. Because there is no "crimping" of the in-plane fibers as in a standard woven matrix, the straightness of the presently disclosed scaffolds decreases buckling of individual fibers and significantly improves their strength and stiffness properties under both compressive and tensile stresses.

An advantage of the presently disclosed weaving technique is that each fiber can be selected individually and woven into a construct. Using this method of assembly, customized structures can be easily created by selectively placing different constituent fibers (e.g., fibers of various material composition, size, and/or coating/treatment) throughout the scaffold. In this manner, physical and mechanical properties of the scaffold can be controlled (i.e., pore sizes can be selected, directional properties can be varied, and discreet layers can be formed). Using this technique, the inhomogeneity and anisotropy of various tissues can be reproduced by constructing a scaffold that mimics the normal stratified tissue network using a single, integral scaffold.

Setting of the yarn systems can be done via any of a number of art-recognized techniques, including but not limited to ultrasonication, a resin, infrared irradiation, heat, or any combination thereof. Setting of the yarn systems within the scaffold in this manner provides cuttability and suturability. Sterilization can be performed by routine methods including, but not limited to autoclaving, radiation treatment, hydrogen peroxide treatment, ethylene oxide treatment, and the like.

Representative methods for making three-dimensional textile structures are also disclosed in U.S. Pat. Nos. 5,465,760 and 5,085,252, the contents of each of which are incorporated herein by reference in their entireties. The following patent publications are also incorporated herein by reference in their entireties: PCT International Patent Application Publication WO 01/38662 (published May 31, 2001); PCT International Patent Application Publication WO 02/07961 (published Jan. 31, 2002); U.S. Patent Application Publication 2003/0003135 (published Jan. 2, 2003), and PCT International Patent Application Serial No. PCT/US06/14437, filed Apr. 18, 2006.

III.C. Consolidation of Fiber Scaffolds with Cell-Seeded Hydrogel

As discussed herein above, the presently disclosed subject matter provides in some embodiments a 3-D woven fiber scaffolds for use in joint replacement. The scaffold can be used in its native form, as a composite material in combination with other materials, as an acellular (non-viable) matrix, or combined with cells (such as but not limited to ADS and/or ADS-derived cells) and/or growth modulating materials (e.g., growth factors) for use in repair, regeneration, and/or replacement of diseased or traumatized tissue (e.g., a joint) and/or tissue engineering applications. An advantage of the presently disclosed subject matter is the ability to produce biomaterial scaffolds and composite matrices that have precisely defined mechanical properties that can be inhomogeneous (vary with site), anisotropic (vary with direction), nonlinear (vary with strain), and/or viscoelastic (vary with time or rate of loading). By combining a fiber-based scaffold with a biocompatible resin or matrix, another advantage of the composite matrix is that the microenvironment of embedded cells can be controlled to promote appropriate cell growth and/or activity while providing for the prescribed mechanical properties. These characteristics can arise from the combination of the two components.

In some embodiments, the fiber scaffold is mixed with cells (such as but not limited to ADS or ADS-derived cells) and crosslinked to form a hydrogel matrix containing the cells before or after implantation into the body. The scaffold functions to provide a template for the integrated growth and differentiation of the desired tissue. In some embodiments, a polymer forms the hydrogel within the body upon contact with a crosslinking agent. A hydrogel is defined as a substance formed when an organic polymer (natural or synthetic) is crosslinked via covalent, ionic or hydrogen bonds to create a three-dimensional open-fiber scaffold structure which entraps water molecules to form a gel. Naturally occurring and synthetic hydrogel forming polymers, polymer mixtures and copolymers can be utilized as hydrogel precursors. See, for example, U.S. Pat. No. 5,709,854 and WO 94/25080.

Hydrogels can be classified into two broad categories: reversible or physical and irreversible or chemical. The networks in physical gels are held together by molecular entanglements and/or secondary forces including ionic, hydrogen bonding or hydrophobic forces. Physical hydrogels are characterized by significant changes in the rheological properties as a function of temperature, ionic concentration, and dilution. Chemical gels, also called permanent gels, are characterized by chemically crosslinked networks. When crosslinked, these gels reach an equilibrium swelling level in aqueous solutions which depends mainly on the crosslink density.

The preparation of hydrogels can be achieved by a variety of methods well known to those of ordinary skill in the art. Physical gels can be formed by: heating or cooling certain polymer solutions (cool agarose, for example), using freeze-thaw cycles to form polymer microcrystals, reducing the solution pH to form a hydrogen-bonded gel between two different polymers in the same aqueous solution, mixing solutions of a polyanion and a polycation to form a complex coacervate gel, gelling a polyelectrolyte solution with a multivalent ion of opposite charge, reticulation of linear polymers, grafting of synthetic polymers onto naturally occurring macromolecules, and chelation of polycations (Hoffman (2000) *Advanced Drug Delivery Reviews*, 43:3-12). Chemical gels can be created by crosslinking polymers in the solid state or in solution with radiation, chemical crosslinkers like glutaraldehyde, or multifunctional reactive compounds. They can also be made by copolymerizing a monomer and a crosslinker in solution, copolymerizing a monomer and a multifunctional macromer, polymerizing a monomer within a different solid polymer to form an IPN gel, or chemically converting a hydrophobic polymer to a hydrogel (Hennick and van Nostrum (2002) *Advanced Drug Delivery Reviews*, 54:13-26).

The presently disclosed subject matter, in some embodiments, provides the use of hydrogel precursor materials and non-gelling proteins and polysaccharides as scaffold materials themselves or within the core of the fibers. Hydrogel precursor materials are the same materials as those that form hydrogels, but they are not exposed to the agents or conditions that normally gel the materials, or can be other proteins and polysaccharides that form gels but not hydrogels. For example, alginate salts, such as sodium alginate, are gelled in the presence of divalent cations, such as calcium, while other materials create hydrogels via a change in pH or temperature. Certain embodiments of the presently disclosed subject matter comprise the use of precursor materials that are never gelled. Other embodiments of the presently disclosed subject matter comprise the use of precursor materials in the fabrication process that later can form gels or hydrogels. The formation of gels or hydrogels in the fiber layer can take place as a part of the fiber fabrication process, after the fiber has been fabricated, or after the application of an appropriate type of external stimuli, including placing the fiber in vitro or in vivo. The terms "gel" or "hydrogel" as used herein is intended to include the formed gel or hydrogel as well as the appropriate precursor molecules involved in the formation of gels and hydrogels.

An exemplary method for combining the fiber-based scaffolds with a gel matrix is via the utilization of a vacuum-assisted molding process. Particularly, the technique utilizes vacuum pressure to draw the gel while still in its liquid form into the 3-D fiber scaffold, effectively filling the pore spaces and encapsulating the fibers. Once the gel has completely infused the scaffold, it is solidified by an appropriate cross-linking method to form the composite construct. In some embodiments, cells and/or growth promoting materials are seeded into the scaffolds by mixing them into a liquid gel prior to infusion into a scaffold.

Thus, the 3-D fiber performs, which in some embodiments are 3-D orthogonally woven fiber performs, can be infiltrated with a cell-seeded or acellular gel material to form a composite construct or bioartificial implant. In some embodiments, the cells can be primary cells (e.g., chondrocytes, osteoblasts, fibroblasts, etc.) and/or undifferentiated progenitor cells (e.g., stem cells, including but not limited to ADS cells). The gel biomaterial can be one of many different types of crosslinkable, photocrosslinkable, temperature sensitive, and/or other gel that can sustain cell growth and provide mechanical function to the scaffold. Possible gels include fibrin, alginate, agarose, elastin, chitosan, collagen, etc.

In some embodiments, to form the fiber scaffold, the cells are introduced onto the scaffold such that they permeate into the interstitial spaces therein. For example, the matrix can be soaked in a solution or suspension containing the cells, or they can be infused or injected into the matrix. In some embodiments, a hydrogel is formed by crosslinking a suspension comprising the fiber and the inventive cells dispersed therein. This particular method of formation permits the cells to be dispersed throughout the fiber scaffold, facilitating more even permeation of the fiber scaffold with the cells. As would be readily apparent to one of ordinary skill in the art, the composition can include mature cells of a desired phenotype or precursors thereof, particularly to potentate the induction of the inventive stem cells to differential appropriately within the fiber scaffold (e.g., as an effect of co-culturing such cells within the fiber scaffold).

In some embodiments, cells can be employed to seed the scaffold, which provides a template for the integrated growth and differentiation into tissue capable of substantially functioning as cartilage and bone. By forming an integrated "bone-cartilage" construct in the shape of a joint (e.g., a hip) outside the body, the implant can adhere to the bone surface of the joint and integrate appropriately. As would be readily apparent to one of skill in the art, cell types, such as ADS or ADS-derived cells, mesenchymal stem cells, primary chondrocytes, or osteoblasts are useful for these applications.

In some embodiments, the scaffold can be coated on one or more surfaces, before or after consolidation with a gel and/or cells, with a material to improve the mechanical, tribological, or biological properties of the composite. Such a coating material can be resorbable or non-resorbable and can be applied by dip-coating, spray-coating, electrospinning, plasma spray coating, and/or other coating techniques. The material can be a single or multiple layers or films. The material can also comprise randomly aligned or ordered arrays of fibers. In some embodiments, the coating can comprise electrospun nanofibers. The coating material can be selected from the group including, but not limited to polypropylene, polyester, polytetrafluoroethylene (PTFE), expanded PTFE (ePTFE), polyethylene, polyurethane, polyamide, nylon, polyetheretherketone (PEEK), polysulfone, a cellulosic, fiberglass, an acrylic, tantalum, polyvinyl alcohol, carbon, ceramic, a metal, polyglycolic acid (PGA), polylactic acid (PLA), polyglycolide-lactide, polycaprolactone, polyethylene glycol) (PEG), polydioxanone, polyoxalate, a polyanhydride, a poly(phosphoester), catgut suture, collagen, silk, chitin, chitosan, hydroxyapatite, bioabsorbable calcium phosphate, hyaluronic acid, elastin, lubricin, and combinations thereof.

In some embodiments a smooth surface coat on the scaffold is thus provided if needed. In some embodiments, the surface coat can increase durability and/or reduce friction of and/or at the surface.

In some embodiments, a fiber scaffold can be employed in any suitable manner to facilitate the growth and generation of the desired tissue types or structures. For example, the scaffold can be constructed using three-dimensional or stereotactic modeling techniques. Thus, for example, a layer or domain within the scaffold can be populated by cells primer for one type of cellular differentiation, and another layer or domain within the scaffold can be populated with cells primed for a different type of cellular differentiation. As disclosed herein and as would be readily apparent to one of skill in the art, to direct the growth and differentiation of the desired structure, in some embodiments, the scaffold can be cultured ex vivo in a bioreactor or incubator, as appropriate. In some embodiments, the structure is implanted within the subject directly at the site in which it is desired to grow the tissue or structure. In further embodiments, the scaffold can be grafted on a host (e.g., an animal such as a pig, baboon, etc.), where it can be grown and matured until ready for use, wherein the mature structure is excised from the host and implanted into the subject.

Thus, provided in some embodiments is a novel scaffold for the growth of tissues/organs both in vitro and in vivo. In particular embodiments, provided is a biodegradable scaffold of multiple layers made preferably with collagen or collagen composite material to be placed in either a bioreactor or a directly into a living bio-organism for the purpose of replacing a damaged and/or missing organ such as bone, wherein the scaffold comprises mechanical structures for stimulating cells.

In some embodiments, the presently disclosed subject matter provides methods for producing an implant for use in joint resurfacing. In some embodiments, the method comprises forming a three-dimensional fiber scaffold, the scaffold comprising at least three systems of fibers; wherein (i) two of the three fiber systems define an upper layer, a lower layer and a medial layer between the upper layer and the lower layer within the three-dimensional fiber scaffold; (ii) one of the at least three fiber systems interconnects the upper layer, the lower layer and the medial layer; and (iii) the at least three fiber systems each comprise a biocompatible material. One or more cells can be disposed in the fiber scaffold such that the cells/matrix construct can develop into tissue capable of substantially functioning as bone, cartilage, or bone and cartilage. It is to be understood that the fiber scaffold or one or more of the fiber systems can provide one or more characteristics of joint to be replaced upon implantation.

In some embodiments, the scaffold, before or after seeding with cells, is molded into the appropriate shape using any standard manufacturing methods including, but not limited to block molding, shape molding, vacuum molding, press molding, compression molding, and combinations thereof.

In some embodiments, a portion or all of the cells seeded in the scaffold are killed (i.e. devitalized) and/or removed prior to implantation. The scaffold can also be treated with DNase, RNase, and/or other enzymes to degrade and/or remove any nucleic acids or genetic material before implantation. Thus, in some embodiments an artificial "tissue" derived from the cell-seed scaffold is provided.

The presently disclosed subject matter also provides methods for replacing a predetermined joint in a subject. In some embodiments, the method comprises (a) providing a joint replacement implant comprising: (i) a three-dimensional fiber scaffold formed of at least three systems of fibers, wherein (1) two of the three fiber systems define an upper layer, a lower layer and a medial layer between the upper layer and the lower layer within the three-dimensional fiber scaffold; (2) one of the at least three fiber systems interconnects the upper layer, the lower layer and the medial layer; and (3) the at least three fiber systems each comprise a bio-compatible material; and (ii) one or more cells that can develop into tissue capable of substantially functioning as bone, cartilage, or bone and cartilage, wherein the fiber scaffold, or one or more of the fiber systems, provide one or more characteristics of the predetermined joint upon implantation; and (b) implanting at a site of the predetermined joint in the subject the implant provided in step (a) to thereby replace a joint in the subject. In some embodiments, the predetermined joint is selected from the group consisting of a hip joint, a knee joint, a shoulder joint, an ankle joint, and an elbow joint, although the methods and compositions disclosed herein are not restricted to just these joints.

IV. BIOREACTOR FOR TISSUE GROWTH AND DIFFERENTIATION

In some embodiments, a bioreactor is used to enhance growth and differentiation of the cells. The bioreactor can enhance tissue differentiation by controlling the temperature, carbon dioxide, oxygen, and nitrogen concentrations, physicochemical environment (e.g., pH, oxygen tension, osmolarity), perfusion, and mechanical loading environment. The bioreactor simultaneously can provide dynamic compressive loading to the joint replacement implants as they grow in vitro.

Thus, as is known to those skilled in the art, bioreactors help in establishing spatially uniform cell distribution on three-dimensional scaffolds, maintaining desired concentrations of gases and nutrients in the culture medium, providing sufficient mass transfer to growing tissues, and exposing developing tissues to physical stimuli.

For example, one or more ADS and/or ADS-derived cells can be grown and/or differentiated in the bioreactor in any suitable cell culture medium. Typically, cell culture media comprise a base medium such as Dulbecco's Modified Eagle's Medium (DMEM) and/or Ham's Nutrient Mixture F12 (F12) medium supplemented with one or more additives selected from the group consisting of an animal serum (e.g., bovine serum) or a reduced serum supplement (e.g., OPTI-MEM® I reduced serum medium supplement, Invitrogen Corp., Carlsbad, Calif., United States of America), an antibiotic (e.g., penicillin and/or streptomycin), and one or more amino acids such as glutamine. Other additives that can be employed are known to those skilled in the art, and can include insulin/transferrin/selenium supplement (ITS, available from Invitrogen Corp., Carlsbad, Calif., United States of America), essential and non-essential amino acids, salts, buffers, and peptides and polypeptides such as growth factors, cytokines, etc. Upon a review of the present disclosure, the skilled artisan will understand how to optimize the concentrations of the various components in order to facilitate the growth and/or differentiation of the cells.

In some embodiments, the cell culture medium further comprises a growth modulating material. As used herein, the phrase "growth modulating material" refers to a molecule or group of molecules that individually or in combination promotes the growth, survival, and/or differentiation of the one or more cells that can develop into a tissue of a predetermined site, such as but not limited to bone, cartilage, or both bone and cartilage. Typically, although not exclusively, the growth promoting material can be present in the medium and/or on or in the scaffold on which the one or more cells is growing.

In some embodiments, the implantable composition can be maintained in the bioreactor prior to implantation for a time sufficient to provide tissue comprising tissue capable of replacing tissue at a predetermined site, for example but not limited to bone, cartilage, or both bone and cartilage.

In some embodiments, the bioreactor provides an in vitro environment that embodies chemical and mechanical signals that regulate tissue development and maintenance in vivo. The bioreactor culture vessels can include, but are not limited to, spinner flasks, rotating vessels, a perfused chamber, or a perfused column. The bioreactor thus can have the ability to apply a variety of (mechanical) signals to the cells.

Bioreactors, especially bioreactors used for tissue regeneration processes, are well known. Reference is hereby made, e.g., to U.S. Pat. Nos. 6,306,169, 6,197,575, 6,080,581, 5,677,355, 5,433,909, 5,898,040, and the like, which are hereby incorporated by reference.

V. FORMULATION

The compositions of the presently disclosed subject matter comprise in some embodiments a composition that includes a carrier, particularly a pharmaceutically acceptable carrier. As disclosed herein above, any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, in one example in the range of 0.1 to 10 mg/ml, in another example about 2.0 mg/ml; and/or mannitol or another sugar, for example in the range of about 10 to 100 mg/ml, in another example about 30 mg/ml; and/or phosphate-buffered saline (PBS).

It should be understood that in addition to the ingredients particularly mentioned herein, the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can also be used with additional adjuvants or biological response modifiers including, but not limited to, cytokines and other immunomodulating compounds.

VI. ADMINISTRATION

Administration of the compositions of the presently disclosed subject matter can be by any method known to one of ordinary skill in the art. In some embodiments, suitable methods for administration of the cells of the presently disclosed subject matter include, but are not limited to injection into the target tissue or target site. The term "target tissue" as used herein refers to an intended site for engraftment following administration to a subject.

In some embodiments, the compositions comprise cells present in a matrix (e.g., a gel) within the pores of a fiber scaffold. The fiber scaffold can be implanted at a predetermined site (i.e., a joint) to replace, repair, and/or restore a target tissue and/or structure at the particular site of insertion. In some embodiments, the fiber scaffold can be implanted in a subject to alleviate tissue loss, damage, injury, or combinations thereof.

The fiber scaffolds can be implanted into the subject at the site in need of treatment using standard surgical techniques. In some embodiments, the fiber scaffold is constructed, seeded with cells and cultured in vitro prior to implantation. The cells can be cultured in the device, tested for viability, and then implanted. In some embodiments, the fiber scaffold is constructed, seeded with cells and cultured in vivo after or during implantation. In some embodiments, the scaffold is implanted without cells.

In some embodiments, the fiber scaffolds can be used for delivery of multiple different cell types. The scaffold can be implanted in one or more different areas of the body to suit a desired application.

In addition, there are situations where it could be desirable to use more than one matrix, each implanted at the most optimum time for growth of the attached cells to form a functioning three-dimensional structure from the different matrices.

VII. DOSE

An effective dose of a composition of the presently disclosed subject matter is administered to a subject in need thereof. A "treatment effective amount" or a "therapeutic amount" is an amount of a therapeutic composition (e.g., induced ADS cells in a pharmaceutically acceptable carrier or excipient) sufficient to produce a biologically or clinically relevant response in a subject being treated. The actual number of induced ADS cells, as an example, in the compositions of the presently disclosed subject matter can be varied so as to administer a number of the induced ADS cells that is effective to achieve the desired therapeutic response for a particular subject. The selected dosage level will depend upon several factors including, but not limited to the ability of the induced ADS cells or their progeny to engraft the target tissue, the route of administration, combination with other drugs or treatments, the severity of the condition being treated, and the condition and prior medical history of the subject being treated.

The potency of a composition can vary, and therefore a "treatment effective amount" can vary. However, using standard assay methods, one skilled in the art can readily assess the potency and efficacy of the induced ADS cells of the presently disclosed subject matter, and adjust the therapeutic regimen accordingly. After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

VIII. SUBJECTS

The subjects treated in the presently disclosed subject matter are in some embodiments human subjects, although it is to be understood that the presently disclosed subject matter is effective with respect to all vertebrate animals, including mammals, which are intended to be included in the term "subject". Moreover, a mammal is understood to include any mammalian species in which treatment or prevention of a disease is desirable, particularly agricultural and domestic mammalian species.

More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, for example, poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

IX. KITS

All the essential materials and reagents required for the various aspects of the presently disclosed subject matter can be assembled together in a kit. The kits typically include vials comprising the desired components in close confinement for commercial sale such as in, e.g., injection or blow-molded plastic containers. Irrespective of the number or type of containers, the kits of the presently disclosed subject matter can be typically packaged with instructions for use of the kit components.

As discussed above, the cells, populations, scaffolds, and compositions of the presently disclosed subject matter can be used in tissue engineering and regeneration. The disclosed scaffolds can conveniently be employed as part of a cell culture kit. Accordingly, the presently disclosed subject matter can provide a kit including the presently disclosed scaffolds and one or more other components, such as hydrating agents (e.g., water, physiologically-compatible saline solutions, prepared cell culture media, serum or derivatives thereof etc.), cell culture substrates (e.g., culture dishes, plates, vials, etc.), cell culture media (whether in liquid or powdered form), antibiotic compounds, hormones, and the like. While the kit can include any such ingredients, it can include all ingredients necessary to support the culture and growth of desired cell types upon proper combination. Of course, if desired, the kit also can include cells (typically frozen), which can be seeded into the fiber scaffold as described herein.

By way of example, any of the steps for isolating one of the cell sources disclosed in the presently disclosed subject matter can also provide a kit for isolating such reagents from adipose tissues. The kit can include a device for isolating adipose tissue from a patient (e.g., a cannula, a needle, an aspirator, etc.), as well as a device for separating stem cells (e.g., through methods described herein or through methods commonly known by one of ordinary skill in the art). The kit can be employed, for example, as a bedside source of stem cells that can then be re-introduced from the same individual as appropriate. Thus, the kit can facilitate the isolation of ADS cells for implantation in a patient needing regrowth of a desired tissue type, even in the same procedure. In this respect, the kit can also include a medium for differentiating the cells, such as those set forth herein. As appropriate, the cells can be exposed to the medium to prime them for differentiation within the patient as needed. In addition, the kit can be used as a convenient source of stem cells for in vitro manipulation (e.g., cloning or differentiating as described herein). In some embodiments, the kit can be employed for isolating a fiber scaffold as described herein.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods Using in the Examples

Cell Culture.

hADS cells from three female donors were purchased from Zen-Bio Inc. (Durham, N.C., United States of America). All hADS cells were originally obtained from subcutaneous abdominal adipose tissue, and all donors were non-smokers and non-diabetics. Lot L012202 was derived from a 34 year old donor with BMI of 22.24; L062801 from a 37 year old with BMI of 23.29; and L031502 from a 47 year old with BMI of 29.08. The cells were plated on 225 cm$^2$ culture flasks (Corning, Corning, N.Y., United States of America) at an initial density of 8,000 cells/cm$^2$ in expansion medium.

Expansion medium comprised DMEM/F12 (Cambrex Bio Science, Walkersville, Md., United States of America), 10% FBS (Hyclone, Logan Utah, United States of America), 1% penicillin-streptomycin-fungizone (Invitrogen GIBCO® Corp., Carlsbad, Calif., United States of America), 0.25 ng/ml TGF-β1 (R&D Systems, Minneapolis, Minn., United States of America), 5 ng/ml EGF (Roche Diagnostics, Indianapolis, Ind., United States of America), and 1 ng/ml bFGF (Roche Diagnostics, Indianapolis, Ind., United States of America).

Culture media was replaced every other day, and the cultures were allowed to reach 90% confluence before trypsinizing and replating at 8000 cell/cm$^2$. The hADS cells were passaged to cell stage P4 at which point they were trypsinized off the culture plates and resuspended in 1.2% alginate solution at 5×10$^6$ cells/mL. Using a 1-mL pipetter, the alginate-cell suspension was dropped into a 102 mM CaCl$_2$ solution making spherical alginate beads. Each bead was approximately 0.4 cm in diameter, containing approximately 150,000 cells.

The hADS cells were then cultured in seven different culture conditions for seven days. One of the culture conditions, which served as a control, consisted of DMEM-high glucose (Invitrogen GIBCO® Corp., Carlsbad, Calif., United States of America), 10% FBS, 1% penicillin-streptomycin, and ascorbic-2-phosphate (37.5 µg/ml). For differentiation induction, 1% ITS+ premix (0.62 µg/ml insulin, 0.62 µg/ml transferrin, and 0.62 ng/ml selenium; Collaborative Biomedical, Becton Dickinson, Bedford, Mass., United States of America) was added to the control medium in addition to the growth factors listed in Table 1. The alginate beads were cultured in 24-well tissue culture plates (Corning Life Sciences, Corning, N.Y., United States of America) with three beads per well and with 1 mL of medium in each well. Culture medium was replaced every other day.

TABLE 1

Growth Factor Combinations for ADS Cell Differentiation

| Growth Factors | Group 1 | Group 2 | Group 3 | Group 4 | Group 5 | Group 6 |
|---|---|---|---|---|---|---|
| 100 nM DEX | X | | | | | |
| 10 ng/ml TGF-β1 | X | X | | | | |
| 10 ng/ml TGF-β3 | | | X | X | X | |
| 100 ng/ml IGF-1 | | | | X | X | |
| 500 ng/ml rhBMP-6 | | | | | X | X |

DNA, [$^3$H]-Proline, and [$^{35}$S]-Sulfate Assays.

For the last 24 hours of culture, 10 µCi/mL of [$^3$H]-proline and 5 µCi/mL of [$^{35}$S]-sulfate were added to each of the different culture conditions in order to quantify total protein and GAG synthesis, respectively. After the beads were digested in papain, DNA content (per three beads) was quantified using the PICOGREEN® fluorescent dsDNA assay (Molecular Probes, Eugene, Oreg., United States of America). Radiolabel incorporation was quantified using a scintillation analyzer, and the resulting data were normalized to DNA content. ANOVA was used with Fisher's PLSD post-hoc test to determine statistical significance between the different conditions ($\alpha=0.05$).

RNA Isolation and Real Time PCR.

Following seven days in culture, the hADS cells were released from alginate using a solution of 150 mM NaCl and 55 mM Na Citrate. RNA from these cells as well as from hADS cells frozen down at Day 0 of the experiment was obtained using the RNeasy® Mini kit from Qiagen (Valencia, Calif., United States of America) and was treated with an RNAse-free DNAse (Qiagen). cDNA was synthesized from RNA using ISCRIPT™ reverse transcriptase PCR (Bio-Rad, Hercules, Calif., United States of America).

Using commercially bought primer-probes from Applied Biosystems (Foster City, Calif., United States of America), real time PCR was used to compare the resulting cDNA for five different genes: 18S rRNA (endogenous control), aggrecan, type I collagen, type II collagen, and type X collagen. The amount of cDNA added per real time PCR reaction was standardized to 40 ng cDNA. The $2^{-\Delta\Delta Ct}$ method was used for relative quantification of gene expression Livak and Schmittgen (2001) *Methods* 25:402-408) to compare the effects of the seven different culture conditions on hADS cell gene expression. ANOVA was used with Fisher's PLSD post-hoc test to determine statistical significance between the different conditions ($\alpha=0.05$).

Immunohistochemistry.

After seven days in culture, alginate beads from each of the seven conditions and from each of the three donors were fixed for four hours in a solution of 4% paraformaldehyde, 100 mM sodium cacodylate, and 50 mM BaCl$_2$ (the latter to irreversibly crosslink the alginate matrix) and then washed overnight in a 100 mM sodium cacodylate, 50 mM BaCl$_2$ buffer. The beads were dehydrated with a series of increasing ethanol concentrations. The beads were then cleared with xylene and then embedded in paraffin wax.

Immunohistochemistry was performed on 5 μm sections using monoclonal antibodies to type I collagen (Sigma Chemical Co., St. Louis, Mo., United States of America), type II collagen (II-II6B3 AB, Developmental Studies Hybridoma Bank, The University of Iowa, Iowa City, Iowa, United States of America), type X collagen (Sigma), and chondroitin sulfate (3B3 antibody, gift from Dr. Virginia Kraus, Duke University Medical Center, Durham, N.C., United States of America). DIGEST-ALL™ (Zymed Laboratories, South San Francisco, Calif., United States of America) was used for pepsin digestion on all sections except those stained for chondroitin sulfate. Sections to be stained for chondroitin sulfate were treated with trypsin (Sigma), then with soybean trypsin inhibitor (Sigma), and then with chondroitinase (Sigma) to allow the antibody to interact with a chondroitin-4-sulfate epitope.

HISTOSTAIN®-Plus ES Kit (Zymed) was used on all sections for blocking, secondary antibody staining, and subsequent linking to horseradish peroxidase. Aminoethyl carbazole (Zymed) was used as the enzyme substrate/chromogen. The appropriate positive controls for each antibody were prepared and examined to ensure antibody specificity: porcine cartilage for type II collagen and chondroitin sulfate, deep layer and calcified zone of cartilage for type X collagen, and meniscus for type I collagen. Negative controls showed minimal background staining.

Example 1

DNA Analysis

The growth factor and cytokine combinations disclosed herein resulted in significant differences in hADS cells encapsulated within 1.2% alginate. In order to normalize the [$^3$H]-proline and [$^{35}$S]-sulfate incorporation results and also to evaluate the viability of the cells, dsDNA was measured at the time of encapsulation in alginate and also at day 7, the terminal time point of the study (FIG. 1).

A two-factor ANOVA showed significant DNA differences between donors and growth factor conditions as well as an interactive effect between the donor and growth factor combination (p<0.0001). A Fisher's PLSD post hoc comparison also demonstrated significant differences between all conditions except in the following conditions (p>0.05): control medium and TGF-β3+IGF-I; TGF-β1 and TGF-β3; and TGF-β3+IGF-I+BMP-6 and BMP-6.

Example 2

Biosynthetic Activity

Significant differences in biosynthetic activity were also observed (see FIGS. 2A and 2B). As with the DNA data, a two-factor ANOVA showed significant differences between donors and growth factor conditions as well as an interactive effect between the donor and growth factor combination (p<0.0001). Notably, [$^3$H]-proline incorporation was greatest within the dexamethasone+TGF-β1 group, and this combination resulted in a statistically significant increase in [$^3$H]-proline incorporation compared to the TGF-β1 condition alone (p<0.0001).

The addition of BMP-6 to TGF-β3 and IGF-I also resulted in a significant increase in protein biosynthetic activity compared to the other growth factor combinations using TGF-β1 or TGF-β3 (without dexamethasone) (p<0.0001). All growth factor combinations resulted in significant increases of [$^{35}$S]-sulfate incorporation compared to the control medium alone (p<0.0001). Significant differences in [$^{35}$S]-sulfate incorporation were also noted between the growth factor conditions containing BMP-6 compared to all other conditions (p<0.05).

Example 3

Gene Expression

As measured by quantitative RT-PCR, the growth factor combinations disclosed herein displayed varying capabilities to induce differentiation with hADS cells encapsulated in 1.2% alginate. As has been noted, mRNAs for two positive markers of chondrogenesis were analyzed (aggrecan and collagen II), and mRNAs of two negative markers of chondrogenesis were analyzed (collagen I and collagen X). The results are expressed as relative quantification of mRNA levels compared to cells at the time of encapsulation (Day 0). As an internal endogenous control for each gene transcript, expression of 18s rRNA was also measured. Again, the data are represented using the $2^{-\Delta\Delta Ct}$ method (Livak & Schmittgen, (2001) *Methods* 25:402-408), where the levels of 18S are used to normalize the amount of mRNA transcript for each gene in the controls (Day 0 cells) and the experimental groups at Day 7. The resulting data represent the fold increase or decrease in gene expression for each gene transcript relative to Day 0 cells (FIGS. 3-6). For all of the genes studied (FIG. 3-6), two factor ANOVA analyses revealed significant effects of both donor and growth factor conditions as well as an interactive effect between donor and growth factor conditions (p<0.0001).

For aggrecan gene expression, only the BMP-6 condition resulted in statistically significant differences in gene expression versus all other conditions (p<0.0001). The addition of BMP-6 to the control medium resulted in an average increase in aggrecan gene expression across the 3 donors of approximately 200 fold. Interestingly, this same statistically significance increase in aggrecan gene transcript compared to all other conditions was not noted in the condition in which BMP-6 was added to the culture along with TGF-β3 and IGF-I.

The addition of BMP-6 and TGF-β3 alone also resulted in a significant increase in col1a1 gene expression over Day 0 controls (p<0.05). Compared to the control medium control group at seven days, the cocktail including TGF-β3, IGF-I, and BMP-6 resulted in significant upregulation of col1a1 gene expression (p<0.0001), whereas the addition of BMP-6 alone did not. All conditions containing TGF-β1 or TGF-β3 and not BMP-6 demonstrated decreased COL1A1 gene expression when compared to the cocktail containing TGF-β3, IGF-I, and BMP-6 (p<0.0001). Interestingly, however, no significant differences were observed in comparing these same TGF-β conditions to the BMP-6 alone condition. Along these same lines, the cocktails containing TGF-β3 and IGF-I as well as the group containing TGF-β3, IGF-I, and BMP-6 were statistically different than the condition containing BMP-6 alone (p<0.05).

Compared to Day 0 controls, the addition of BMP-6 in the two conditions or the condition containing TGF-β3 alone resulted in a significant upregulation of col2a1 gene expression (p<0.05). However, of these three conditions, only the condition containing TGF-β3, IGF-I, and BMP-6 resulted in a significant increase in gene expression relative to the Day 7 control medium condition (p 0.0017). The two BMP-6 conditions also resulted in a significant upregulation of COL2A1 compared to either of the conditions containing TGF-β1 (p<0.001). Comparing TGF-β1 and TGF-β3, TGF-β3 shows a significant increase in COL2A1 gene expression relative to TGF-β1+dexamethasone and relative to TGF-β3+IGF-I suggesting that either dexamethasone or IGF-1 inhibits COL2A1 when used in combination with TGF-β3 (p<0.05). Interestingly, the addition of BMP-6 restored the inhibitory nature of IGF-I (p<0.05).

For COL10A1 gene expression, all of the conditions containing a TGF-β isoform resulted in a significant increase in COL10A1 mRNA transcript levels compared to either the Day 0 control cells or the control medium at Day 7. Conversely, the addition of exogenous BMP-6 significantly reduced the levels of COL10A1 transcript levels after seven days in culture relative to the Day 0 control cells and the TGF-β isoform conditions.

Example 4

Immunohistochemistry

Figure 7:
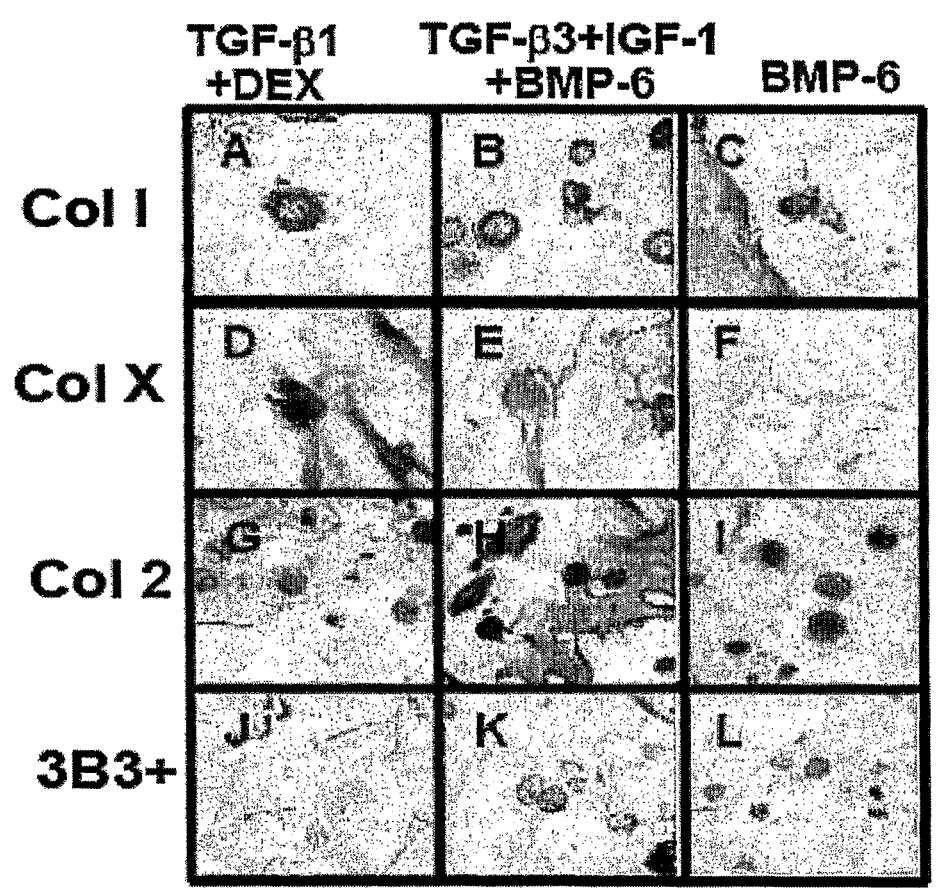
FIGS. 7A-7L depict photographs of the results of immunohistochemistry of hADS cell-alginate beads after 7 days in culture. All photographs were at 63× magnification.

The same trends existing in the gene expression data were also evident in the immunohistochemistry results. The negative controls exhibited minimal background staining. In addition, the immunohistochemistry results from the control showed insignificant staining for all antibodies studied. The most robust and interesting trends were seen in the TGF-β1+dexamethasone and the two BMP-6 groups as shown in FIG. 7.

Specifically, more intense staining for chondroitin 6-sulfate (3B3 epitope) is seen with the BMP-6 group compared to the TGF-β1+dexamethasone condition. This same trend was also observed with the collagen II antibody (II-II6B3). The expression of collagen I showed little qualitative differences across the groups, though collagen I is noted in the pericellular and extracellular matrix with all the growth factors employed; whereas the addition of BMP-6 alone resulted in a significant decrease in staining intensity for collagen X compared to the TGF-β1+dexamethasone condition.

Discussion of Examples 1-4

Figure 3:
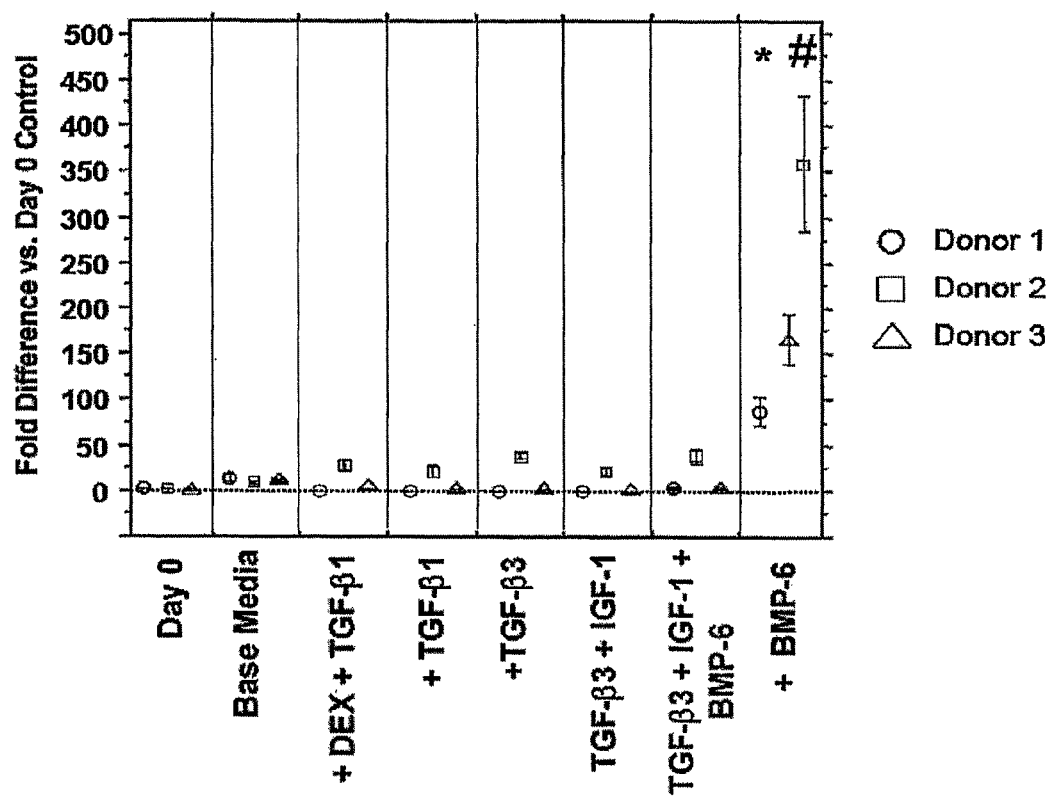
FIGS. 3-6 depict gene expression analyses for AGC1 (FIG. 4; ≥4/condition/donor. *, $p<0.0001$ relative to Day 0 Control. #, $p<0.0001$ relative to Base Medium at Day 7); COL1A1 (FIG. 5; ≥4/condition/donor. *, $p<0.05$ relative to Day 0 Control. #, $p<0.0001$ relative to Base Medium at Day 7); COL2A1 (FIG. 6; ≥4/condition/donor. *, $p<0.05$ relative to Day 0 Control. #, $p<0.05$ relative to Base Medium at Day 7); and COL10A1 (FIG. 7; ≥4/condition/donor. *, $p<0.005$ relative to Day 0 Control. #, $p<0.05$ relative to Base Medium at Day 7). For each of FIGS. 4-7, data are presented as mean±S.E.M. For each of FIGS. 4-7, "○", "□", and "Δ" represent Donors 1, 2, and 3, respectively.

The effects of BMP-6 on hADS cells have not previously been described. The presently disclosed subject matter shows that BMP-6 is a strong inducer of a phenotype that has some cartilage characteristics in hADS cells compared to other growth factors. For aggrecan gene expression, the addition of BMP-6 alone, averaged across the three cell donors, resulted in a 205-fold increase in aggrecan gene expression (FIG. 3). Somewhat surprisingly, the control group, which included the base medium with only 10% FBS, showed consistent increases in aggrecan gene expression roughly equal (on average) to the other growth factors used in this study. Statistically significant differences were noted with COL1A1 gene expression between the conditions containing BMP-6 and the other conditions.

Figure 4:
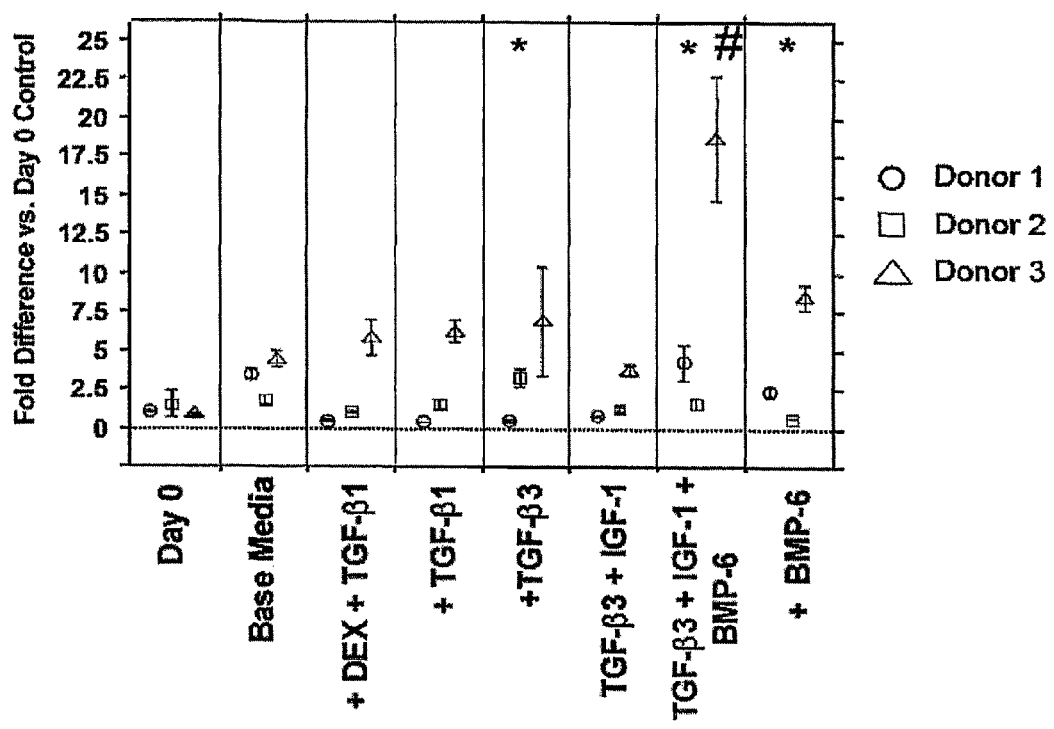
Figure 5:
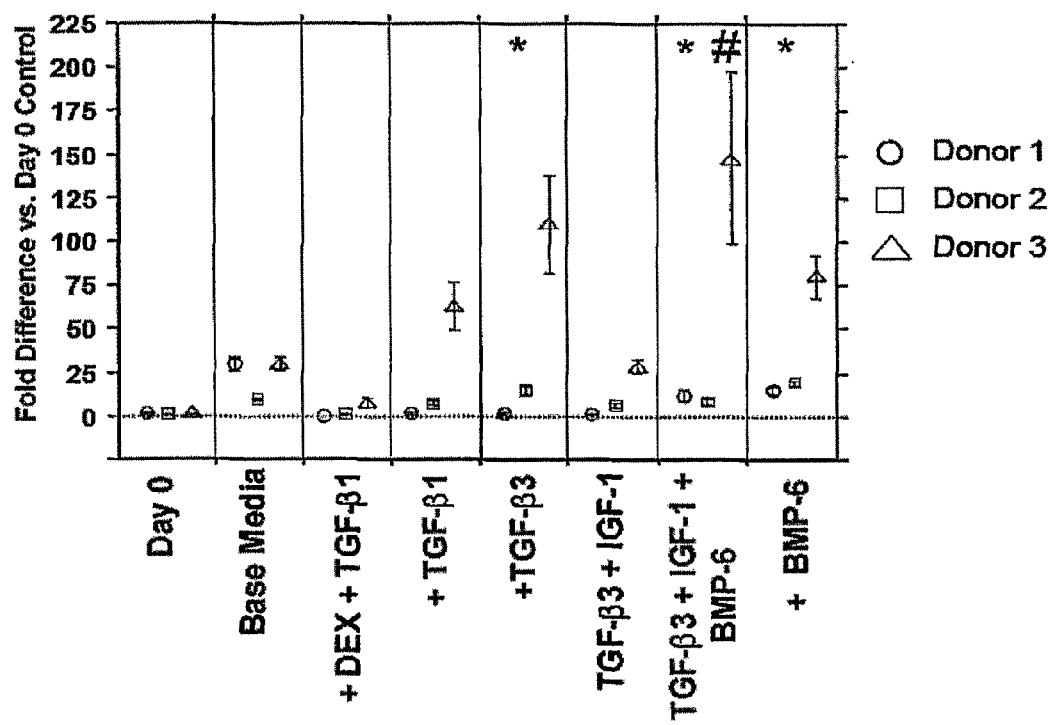

Interestingly, the condition containing TGF-β3, IGF-I, and BMP-6 resulted in a significant increase in COL1A1 gene expression relative to other conditions, while BMP-6 alone, compared to BMP-6 in conjunction with the other two growth factors, showed a decrease in COL1A1 gene expression potentially alluding to synergism between TGF-β3, IGF-I, and BMP-6 in promoting col1a1 gene expression (FIG. 4). BMP-6 also consistently increased COL2A1 gene expression across all 3 donors; this was seen in both the multiple growth factor condition containing BMP-6 as well as BMP-6 alone. The other growth factor combinations were able to induce COL2A1 gene expression in two of the three donors. Again, and somewhat surprisingly, the base medium was also able to induce a consistent increase in COL2A1 gene expression, though this should be viewed in light of a significant decrease in DNA content for this base medium condition over the seven-day time course (FIG. 1).

Figure 6:
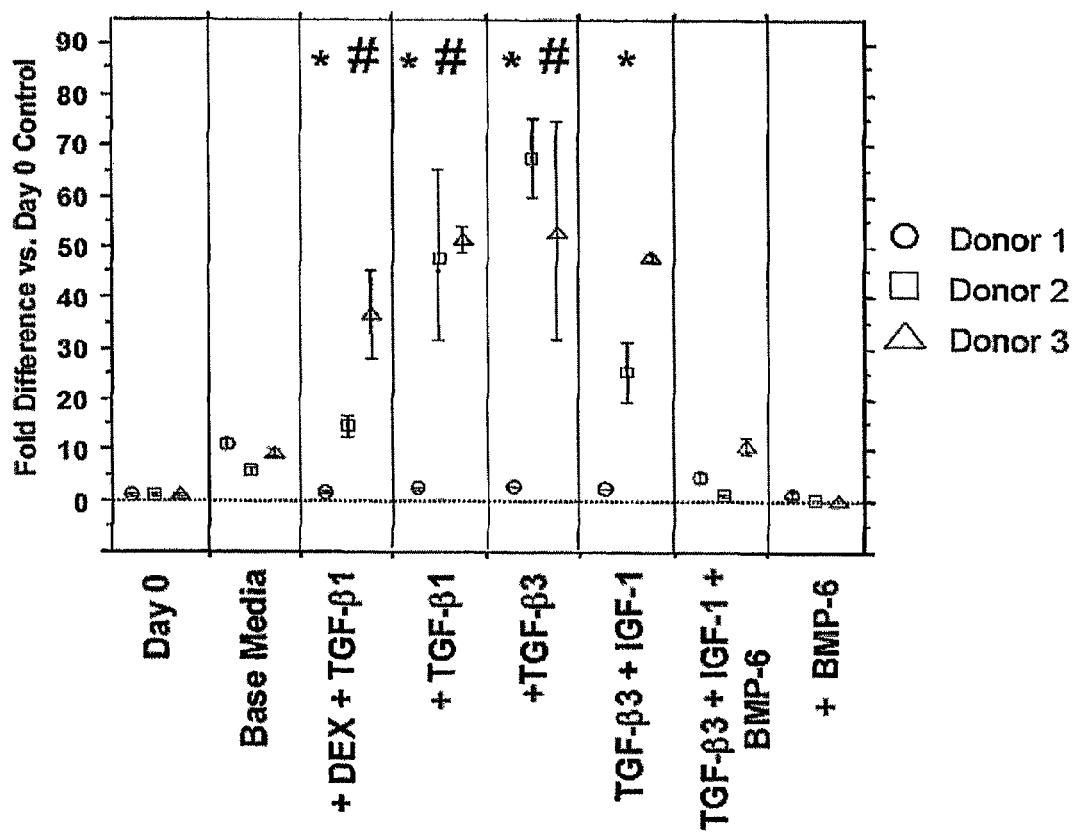

In stark contrast to previous studies in the art (Sekiya et al. (2001) *Biochem Biophys Res Commun* 284:411-418; Sekiya et al. (2002) *Proc Natl Acad Sci USA* 99:4397-4402; Indrawattana et al. (2004) *Biochem Biophys Res Commun* 320:914-919), the results presented herein not only demonstrate BMP-6 as a strong inducer of two chondrogenic markers, aggrecan and COL2A1, but also a strong inhibitor of the hypertrophic/endochondral ossification pathway as measured by significant decreases in COL10A1 gene expression and COL10A1 antibody staining compared to other conditions (FIG. 6 and FIG. 7). One might argue that longer time periods in this study would reveal an increase in COL10A1 gene expression; however, it should be noted that even at seven days in the studies by Sekiya et al., (Sekiya et al. (2001) *Biochem Biophys Res Commun* 284:411-418; Sekiya et al. (2002) *Proc Natl Acad Sci USA* 99:4397-4402 Sekiya et al., 2001; Sekiya et al., 2002), PCR analysis revealed an increase in COL10A1 gene expression relative to the Day 0 controls, which is directly opposite the results disclosed herein. Again, it should be noted that this decrease in the COL10A1 gene expression was also observed in the immunohistochemistry data (e.g., compare FIGS. 7F to 7D and 7E).

Exchanging TGF-β1 for TGF-β3 also did not seem to have a profound effect in promoting a differentiation effect as both isotypes exhibit similar responses across all assays; this result is somewhat inconsistent with other work, which showed that TGF-β was superior to TGF-β1 in inducing chondrogenesis in MSCs (Barry et al. (2001) *Exp Cell Res* 268:189-200). IGF-I also did not seem to have a strong effect in promoting synergism with TGF-β3 and with TGF-β3 and BMP-6; in fact the addition of IGF-1 and TGF-β3 to BMP-6 appears to partially inhibit the response of the cells to BMP-6. One potential explanation would be that both TGF-β3 and IGF-I can initiate multiple signaling pathways different from that of BMP-6 and that downstream events associated with these pathways can somehow compete and inhibit the ability of BMP-6 to promote differentiation.

The most widely used growth cocktail for inducing chondrogenesis includes TGF-β1 and dexamethasone (Johnstone et al. (1998) *Exp Cell Res* 238:265-272) as discussed herein. While this combination of growth factors is able to induce a chondrogenic response in other mesenchymal stem cells, the presently disclosed subject matter demonstrates that this combination of growth factors is less than ideal for promoting chondrogenesis in hADS cells. This condition showed the highest DNA content at Day 7 relative to Day 0 with the levels of DNA staying consistent on average with Day 0 DNA levels (FIG. 1). This TGF-β1+dexamethasone condition also showed the highest [$^3$H]-proline biosynthesis rates over the last 24 hours of culture, indicating metabolically active cells.

Although the highest rates of protein synthesis and highest levels of DNA content are observed in the TGF-β1+dexamethasone condition, this condition proved to be the weakest inducer of COL2A1 mRNA expression, which was also observed in the collagen 2 immunohistological analysis. Increases in both COL1A1 and COL10A1 gene expression along with a concomitant decrease in both aggrecan gene expression and 3B3 immunohistological staining suggest that this combination can induce an osteogenic phenotype.

Figure 2:
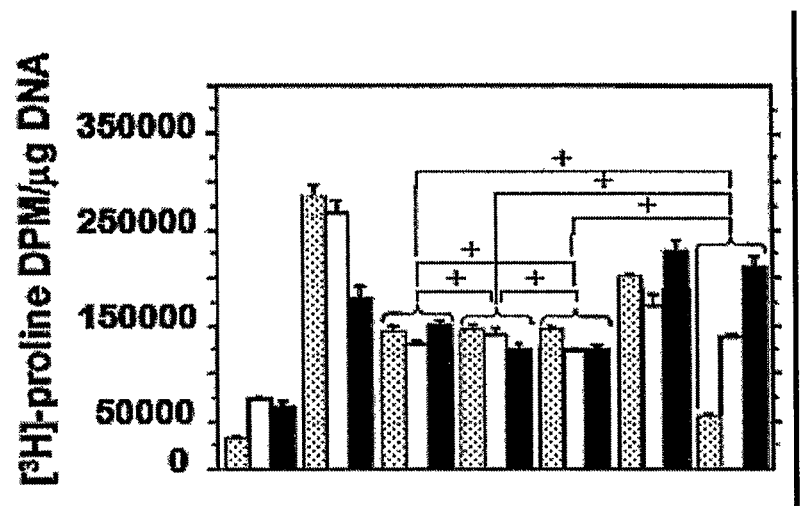
FIGS. 2A and 2B present bar graphs of biosynthetic activity of hADS from 3 donors under various growth factor treatments. [$^3$H]-proline DPM/µg DNA (FIG. 3A) and [$^{35}$S]-sulfate DPM/µg DNA (FIG. 3B) incorporation into protein were determined. The x-axis values for each Figure are the same as in FIG. 2. All comparisons between growth factor conditions are significant at $p<0.05$. "+" indicates non-significance at $p>0.05$ (n≥4/condition/donor). Data are presented as mean±S.E.M.). Patterned bars represent donor 1, white bars represent donor 2, and black bars represent donor 3.
Figure 2:
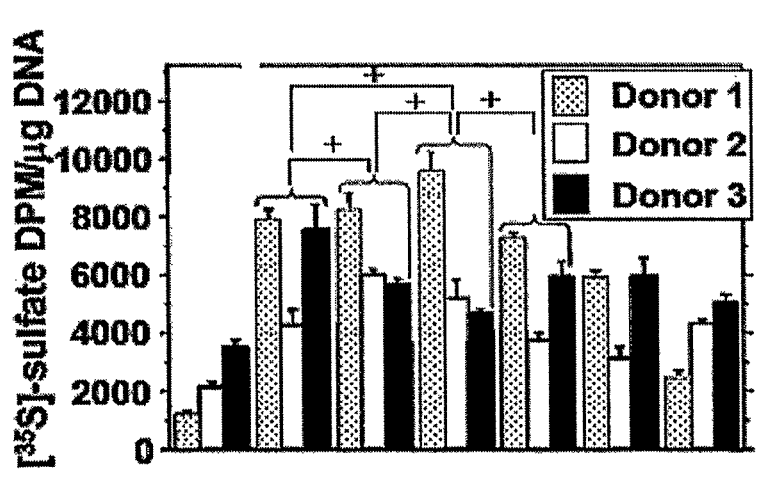

Comparatively, the BMP-6 conditions also maintained higher DNA amounts and biosynthetic activities after seven days across the three donors as compared to the other conditions without dexamethasone (FIGS. 1 and 2). A decrease in COL2A1 gene expression when dexamethasone is added to TGF-β1, compared to the TGF-β1 condition alone, suggests that dexamethasone is somewhat inhibiting COL2A1.

Studies by Boden et al. (Boden et al. (1996) *Endocrinology* 137:3401-3407; Boden et al. (1997) *Endocrinology* 138:2820-2828; Boden et al. (1998) *Endocrinology* 139: 5125-5134; Liu et al. (2004) *Bone* 35:673-681) indicate that BMP-6 is also upregulated by glucocorticoids, suggesting that BMP-6 is required for endochondral ossification and plays a role in bone formation in MSCs. Conversely, the data disclosed herein suggest that BMP-6 does not signal through the same pathway as in MSCs since a different response is observed than that reported for MSCs.

As disclosed herein, hADS cells, respond in a vastly different fashion than MSCs. Most notably and in direct contrast to the effects BMP-6 has on other cell types in inducing a strong osteogenic phenotype, not only does BMP-6 induce a novel phenotype as indicated by strong COL2A1 and aggrecan gene expression and immunohistochemical data, it also appears to inhibit the endochondral ossification pathway as evidenced by the significant decrease in COL10A1 gene expression, also confirmed by immunohistochemistry.

As new paradigms for clinical intervention for musculoskeletal tissue pathology are sought, the present disclosure suggests that hADS cells used in conjunction with BMP-6 can be viable candidates for various remodeling, repair, regrowth, and/or regeneration strategies of various orthopaedic tissues, which serve mechanical functions. Some embodiments include the use of hADS cells that have been induced ex vivo to produce cartilaginous-like tissue and then reimplanted. Some embodiments include a genetic engineering approach in which the gene for either BMP-6 or the BMP-6 receptor could be inserted into the genome of hADS cells and then delivered to the pathological site for in vivo repair/regeneration.

REFERENCES

The references listed below as well as all references cited in the specification are incorporated herein by reference to the extent that they supplement, explain, provide a background for, or teach methodology, techniques, and/or compositions employed herein.

Alam & Cook (1990) *Anal Biochem* 188:245-254.
Awad et al. (2003) *Tissue Eng* 9:1301-1312.
Awad et al. (2004) *Biomaterials* 25:3211-3222.
Barry et al. (2001) *Exp Cell Res* 268:189-200
Blanpain et al. (2004) *Cell* 118:635-648.
Boden et al. (1996) *Endocrinology* 137:3401-3407.
Boden et al. (1997) *Endocrinology* 138:2820282-8.
Boden et al. (1998) *Endocrinology* 139:5125-5134.
Bonadio et al. (1999) *Nat. Med.* 5:753-759.
Boskey et al. (2002) *J Cell Biochem* 84:509-519.
Breinan et al. (1997) *J Bone Joint Surg Am* 79:1439-1451.
Breinan et al. (2001) *J Orthop Res* 19:482-492.
Brittberg (1999) *Suppl Clin Orthop Relat Res* 367:S147-S155.
Brittberg et al. (1994) *N Engl J Med* 331:889-895.
Brittberg et al. (1996) *Clin Orthop Relat Res* 326:270-283.
Byk et al. (1998) *Human Gene Therapy* 9:2493-2502.
Cheng et al. (2003) *J Bone Joint Surg Am* 85-A:1544-1552.
Chu et al. (1995) *J. Biomed. Mater. Res.* 29:1147-1154.
Cubitt et al. (1995) *Trends Biochem Sci* 20:448-455.
De Uqarte et al. (2003) *Immunol Lett* 89:267-270.
De Ugarte et al. (2003) *Cells Tissues Organs* 174:101-109.
Erickson et al. (2001) "Adipose tissue-derived stromal cells display a chondrogenic phenotype in culture". 47th Annual Meeting of the Orthopaedic Research Society, San Francisco, Calif., United States of America.
Erickson et al. (2002) *Biochem Biophys Res Commun* 290: 763-769.
Evans and Kaufman (1981) *Nature* 292:154-156.
Ferguson et al. (2004) *J Orthop Res* 22:687-696.
Fukumoto et al. (2003) *Osteoarthritis Cartilage* 11:55-64.
Furukawa et al. (1980) *J Bone Joint Surg Am* 62:79-89.
GENBANK® Accession Nos. NM_001718; NP_001709; NP_001835; and P16112.
Gillogly et al. (1998) *J Orthop Sports Phys Ther* 28:241-251.
Gitelman et al. (1994) *J Cell Biol* 126:1595-1609.
Gitelman et al. (1995) *Cell Growth Differ* 6:827-836.
Grimsrud et al. (1999) *J Bone Miner Res* 14:475-482.
Grimsrud et al. (2001) *J Orthop Res* 19:18-25.
Gruber et al. (2000) *Cytokine* 12:1630-1638.
Gruber et al. (2003) *Cytokine* 23:133-137.
Hendrickson et al. (1994) *Orthop. Res.* 12:485-497.
Hennick and van Nostrum (2002) *Advanced Drug Delivery Reviews*, 54:13-26.
Hoffman (2000) *Advanced Drug Delivery Reviews*, 43:3-12.
Huang et al. (2002) *Plast Reconstr Surg* 1033-41; discussion 109:1042-1043.
Huang et al. (2004) *Plast Reconstr Surg* 113:585-594.
Hunziker (2002) *Osteoarthritis Cartilage* 10:432-463.
Indrawattana et al. (2004) *Biochem Biophys Res Commun* 320:914-919.
Ito et al. (1999) *Biochim Biophys Acta* 1451:263-270.
Iwasaki et al. (1997) *Mech Dev* 69:197-202.
Jackson et al. (2001) *Suppl Clin Orthop Relat Res* 391:S14-S25.
Johnstone et al. (1998) *Exp Cell Res* 238:265-272.
Kang et al. (2004). *Gene Ther* 11:1312-1320.
Kim et al. (1991) *J Bone Joint Surg Am* 73:1301-1315.
Kogler et al. (2004) *J Exp Med* 200:123-135.
Liu et al. (2004) *Bone* 35:673-681.
Livak and Schmittgen (2001) *Methods* 25:402-408.
Lyons et al. (1989) *Genes Dev* 3:1657-1668.
Mackay et al. (1998) *Tissue Eng* 4:415-428.
Martin (1981) *Proc Natl Acad Sci USA* 78:7634-7638.
Minas and Nehrer (1997) *Orthopedics* 20:525-538.
Mitchell and Shepard (2004) *Clin Orthop Relat Res* 423:3-6.
Nehrer et al. (1999) *Clin Orthop Relat Res* 365:149-162.
Perka et al. (2000) *J. Biomed. Mater. Res.* 49:305-311.
Pittenger et al. (1999) *Science* 284:143-147.
Probst et al. (2000) *BJU Int.*, 85(3), 362-367.
Robertson (1986) *Trends Genet* 2:9-13.
Rose and Botstein (1983) *Methods Enzymol* 101:167-180.
Safford et al. (2002) *Biochem Biophys Res Commun* 294: 371-379.
Safford et al. (2004) *Exp Neurol* 187:319-328.
Sammons et al. (2004) *Stem Cells Dev* 13:273-280.
Scharfmann et al. (1991) *Proc Natl Acad Sci USA* 88:4626-4630.

Sechriest et al. (2000) *J. Biomed. Mater. Res.* 49:534-541
Sekiya et al. (2001) *Biochem Biophys Res Commun* 284: 411-418.
Sekiya et al. (2002) *Proc Natl Acad Sci USA* 99:4397-402.
Sen, et al. (2001) *Journal of Cellular Biochemistry*, 81:312-319.
Shapiro et al. (1993) *J Bone Joint Surg Am* 75:532-553.
Solloway et al. (1998) *Dev Genet* 22:321-339.
Sommer et al. (1999) *Calcif. Tissue Int.* 64:45-49.
Tew et al. (2000) *Arthritis Rheum* 43:215-225.
Vortkamp et al. (1996) *Science* 273:613-622.
Wakitani et al., (1995) *Muscle Nerve,* 18(12), 1417-1426
Wickham et al. (2003) *Clin Orthop Relat Res* 421:196-212.
Williams et al. (1993) *J Clin Invest* 92:503-508.
Williams et al. (1999) *The American Surgeon* 65:22-26.
Yoo et al. (1998) *J Bone Joint Surg Am* 80:1745-1757.
Zuk et al. (2001) *Tissue Eng* 7:211-228.
Zuk et al. (2002) *Mol Biol Cell* 13:4279-4295.
PCT International Patent Application Publication WO 94/25080.
PCT International Patent Application Publication WO 96/22362.
PCT International Patent Application Publication WO 97/32033.
PCT International Patent Application Publication WO 97/47763.
PCT International Patent Application Publication WO 98/43679.
PCT International Patent Application Publication WO 01/38662.
PCT International Patent Application Publication WO 02/07961.
U.S. Patent Application Publication 2003/0003135.
U.S. Pat. No. 5,085,252.
U.S. Pat. No. 5,433,909.
U.S. Pat. No. 5,453,357.
U.S. Pat. No. 5,465,760.
U.S. Pat. No. 5,591,625.
U.S. Pat. No. 5,670,372.
U.S. Pat. No. 5,677,355.
U.S. Pat. No. 5,690,926.
U.S. Pat. No. 5,709,854.
U.S. Pat. No. 5,827,735.
U.S. Pat. No. 5,827,740.
U.S. Pat. No. 5,843,780.
U.S. Pat. No. 5,898,040.
U.S. Pat. No. 5,906,934.
U.S. Pat. No. 5,908,784.
U.S. Pat. No. 6,080,581.
U.S. Pat. No. 6,090,622.
U.S. Pat. No. 6,197,575.
U.S. Pat. No. 6,200,806.
U.S. Pat. No. 6,242,252.
U.S. Pat. No. 6,306,169.
U.S. Pat. No. 6,387,367.
U.S. Pat. No. 6,777,231.
U.S. Pat. No. 6,872,389.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A joint resurfacing implant adapted to replace at least a portion of an articulating surface of a predetermined joint of a subject, the implant comprising a woven fibrous biocompatible three-dimensional scaffold formed of a biocompatible textile molded into a three-dimensional shape prior to implantation that corresponds to the portion of the articulating surface of the predetermined joint being replaced to resurface and re-establish the joint anatomy of the portion of the articulating surface of the predetermined joint upon implantation.

2. The joint resurfacing implant of claim 1, wherein the textile is formed of fibers selected from the group consisting of a monofilament fiber, a multifilament fiber, a hollow fiber, a fiber having a variable cross-section along its length, or a combination thereof.

3. The joint resurfacing implant of claim 1, wherein said scaffold is a three-dimensional fiber scaffold selected from the group consisting of three orthogonally woven fiber systems, a plurality of braided fiber systems, a plurality of circular woven fiber systems, or combinations thereof.

4. The joint resurfacing implant of claim 1, wherein the three-dimensional scaffold defines a plurality of interstices throughout said scaffold, the interstices having a pore size ranging from about 1 μm to about 1,000 μm.

5. A joint resurfacing implant adapted to replace at least a portion of an articulating surface of a predetermined joint of a subject, the implant comprising:
 (a) a woven fibrous three-dimensional scaffold comprising a biocompatible textile material molded into a three-dimensional shape prior to implantation that corresponds to the portion of the articulating surface of the predetermined joint being replaced to re-establish the joint anatomy; and
 (b) one or more cells, wherein the scaffold and one or more cells are adapted to resurface at least the portion of the articulating surface of the predetermined joint after implantation.

6. The joint resurfacing implant of claim 5, wherein at least a fraction of the cells are devitalized before implantation.

7. The joint resurfacing implant of claim 5, wherein the biocompatible textile material comprises a material selected from the group consisting of an absorbable material, a non-absorbable material, and combinations thereof.

8. The joint resurfacing implant of claim 7, wherein the non-absorbable material is selected from the group consisting of a polytetrafluoroethylene (PTFE), an expanded PTFE (ePTFE), a polyamide, a nylon, a polysulfone, a cellulosic, an acrylic, tantalum, polyvinyl alcohol, carbon, ceramic, a metal, an acrylic, a polycarbonate, a polyester, a polyether, a poly(ether ketone), a poly(ether ether ketone), a poly(aryl ether ketone), a poly(ether ether ketone ether ketone), a poly(ethylene terephthalate), a poly(methyl (meth)acrylate), a polyolefin, a polysulfone, a polyurethane, a polyethylene, a polypropylene, a poly(vinyl chloride), a carbon fiber reinforced composite, a glass fiber reinforced composite, and combinations thereof.

9. The joint resurfacing implant of claim 7, wherein the absorbable material is selected from the group consisting of a polyglycolic acid (PGA), a polylactic acid (PLA), a polyglycolide-lactide, a polycaprolactone, a polydioxanone, a polyoxalate, a polyanhydride, a poly(phosphoester), catgut suture, collagen, silk, alginate, agarose, chitin, chitosan, hydroxyapatite, bioabsorbable calcium phosphate, hyaluronic acid, elastin, a polyorthoester, a poly(amino acid), a pluronic/F-12, a poly(ethylene oxide)/poly(ethylene glycol) (PEO/PEG), collagen, gelatin), a blood derivative, plasma, synovial fluid, serum, fibrin, hyaluronic acid, a proteoglycan, elastin, and combinations thereof.

10. The joint resurfacing implant of claim 5, wherein the biocompatible textile material is formed of fibers selected from the group consisting of a monofilament fiber, a multifilament fiber, a hollow fiber, a fiber having a variable cross-section along its length, or a combination thereof.

11. The joint resurfacing implant of claim 5, wherein said scaffold is a three-dimensional fiber scaffold selected from the group consisting of three orthogonally woven fiber systems, a plurality of braided fiber systems, a plurality of circular woven fiber systems, or combinations thereof.

12. The joint resurfacing implant of claim 11, wherein the three dimensional fiber scaffold defines a plurality of interstices throughout said scaffold, the interstices having a pore size ranging from about 1 μm to about 1,000 μm.

13. The joint resurfacing implant of claim 5, wherein the one or more cells are selected from the group consisting of primary cells, undifferentiated progenitor cells, stem cells, and combinations thereof.

14. The joint resurfacing implant of claim 13, wherein the undifferentiated progenitor cells or stem cells are selected from the group consisting of stem or progenitor cells derived from adipose tissue, bone marrow, synovium, muscle, bone, cord, blood, embryos, amniotic fluid, periosteum, and combinations thereof.

15. The joint resurfacing implant of claim 13, wherein the primary cells are selected from the group consisting of chondrocytes, osteoblasts, fibroblasts, fibrochondrocytes, and combinations thereof.

16. The joint resurfacing implant of claim 5, further comprising a biologically active material selected from the group consisting of a growth factor, a cytokine, a chemokine, a collagen, gelatin, laminin, fibronectin, thrombin, lipids, cartilage oligomeric protein (COMP), thrombospondin, fibrin, fibrinogen, Matrix-GLA (glycine-leucine-alanine) protein, chondrocalcin, tenascin, a mineral, an RGD (Arginine-Glycine-Aspartic Acid) peptide or RGD-peptide containing molecule, elastin, hyaluronic acid, a glycosaminoglycan, a proteoglycan, water, an electrolyte solution, and combinations thereof.

17. The joint resurfacing implant of claim 1, wherein the biocompatible three-dimensional scaffold is molded into the three-dimensional shape using block molding, shape molding, vacuum molding, press molding, compression molding or combinations thereof.

18. The joint resurfacing implant of claim 17, wherein the biocompatible three-dimensional scaffold includes a viscous gel infused therethrough, the viscous gel adapted to be cross-linked within the scaffold to maintain the three-dimensional shape.

19. The joint resurfacing implant of claim 3, wherein the fiber systems are settable by ultrasonication, a resin, infrared radiation, heat or any combination thereof.

20. The joint resurfacing implant of claim 5, wherein the three-dimensional scaffold is molded into the three-dimensional shape using block molding, shape molding, vacuum molding, press molding, compression molding or combinations thereof.

21. The joint resurfacing implant of claim 20, wherein the three-dimensional scaffold includes a viscous gel infused therethrough, the viscous gel adapted to be cross-linked within the scaffold to maintain the three-dimensional shape.

22. The joint resurfacing implant of claim 11, wherein the fiber systems are settable by ultrasonication, a resin, infrared radiation, heat or any combination thereof.

* * * * *